US006583251B1

(12) United States Patent
Chaikof et al.

(10) Patent No.: US 6,583,251 B1
(45) Date of Patent: Jun. 24, 2003

(54) MODULAR CYTOMIMETIC BIOMATERIALS, TRANSPORT STUDIES, PREPARATION AND UTILIZATION THEREOF

(75) Inventors: Elliot L. Chaikof, Dunwoody, GA (US); Kacey G. Marra, Atlanta, GA (US); John H. Chon, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/342,922

(22) Filed: Jun. 30, 1999

Related U.S. Application Data

(63) Continuation-in-part of application No. 09/149,098, filed on Sep. 8, 1998, now abandoned.
(60) Provisional application No. 60/091,399, filed on Jun. 30, 1998, provisional application No. 60/101,252, filed on Sep. 21, 1998, and provisional application No. 60/058,194, filed on Sep. 8, 1997.

(51) Int. Cl.⁷ .................................................. C08F 30/02
(52) U.S. Cl. ..................... 526/277; 526/285; 526/310; 424/450; 427/407.1; 428/35.7; 428/402.2
(58) Field of Search ................................ 424/178, 199, 424/450; 427/244, 299, 407.1; 428/35.7, 402.2; 526/277, 285, 310

(56) References Cited

U.S. PATENT DOCUMENTS

| | | | |
|---|---|---|---|
| 4,485,045 A | 11/1984 | Regen | 260/403 |
| 4,560,599 A | 12/1985 | Regen | 428/36 |
| 4,880,883 A | 11/1989 | Grasel et al. | 535/454 |
| 5,288,517 A | 2/1994 | Kanno et al. | 427/244 |
| 5,417,969 A | 5/1995 | Hsu et al. | 424/78 |
| 5,429,618 A | 7/1995 | Keogh | 604/266 |
| 5,755,788 A | 5/1998 | Strauss | 623/11 |

FOREIGN PATENT DOCUMENTS

| | | |
|---|---|---|
| EP | 355847 | 2/1990 |
| JP | 63236731 | 10/1988 |
| WO | 96/21469 | 7/1996 |

OTHER PUBLICATIONS

US 5,556,632, 9/1996, Kohler et al. (withdrawn)
Otani et al., *Biomaterials*, 17(14), 1996, 1387–91.
Santin et al., *Biomaterials*, 17(15), 1996, 1459–67.
Kohler et al., *J.Biomed.Mat.Res.*, 32, 1996, 237–42.
Chen et al., *J.Appl.Poly.Sci.*, 60, 1996, 455–64.
McLean et al., *Thin Solid Films*, 99, 1983, 127–31.
Moore et al., *Macromol.*, 16, 1983, 335–38.
Ohno et al., *Macromol.*, 20, 1987, 929–33.
Campell et al., *Asaio Journal*, 1994, M853–M857.
Chapman, *Langmuir*, 9, 1993, 39–45.
Solletti et al., *Langmuir*, 1, 1996, 5379–86.
Lamparski et al., *J.Am.Chem.Soc.*, 11, 1993, 8096–8102.
Marra et al., "Cytomimetic Biomaterials, 2. In–Situ Polymerization of Phospholipids on a Polymer Surface", *Langmuir*, 13:5697–5701, 1997.
Ueda et al., *Polymer Journal*, 24 (11), 1992, 1259–69.
Marra et al., "Cytomimetic Biomaterials, 1. In–Situ Polymerization of Phospholipids on an Alkylated Surface", Apr. 3, 1997.
Markovich et al., *Anal. Chem.*, 63, 1991, 1851–60.
Ishihara et al., *J. Biomed. Mat. Res.*, 26, 1992, 1543–52.
Ishihara et al., *J. Biomed. Mat. Res.*, 24, 1990, 1069–77.

*Primary Examiner*—Tatyana Zalukaeva
(74) *Attorney, Agent, or Firm*—Greenlee, Winner and Sullivan, P.C.

(57) ABSTRACT

The present invention provides a biocompatible material, comprising a phospholipid or phospholipid derivative comprising various functional groups having specific chemical properties, which can function as a modular surface design unit to be incorporated or appended to a desired substrate on which it is then polymerized, thereby contributing new or specified biochemical characteristics to the polymerized and stabilized biomaterial.

20 Claims, 8 Drawing Sheets

Au-coated wafer    Terpolymer (MTEM,HEA,ACD)    Phospholipid Polymer

MODULAR CYTOMIMETIC BIOMATERIALS, TRANSPORT STUDIES, PREPARATION AND UTILIZATION THEREOF

This application is a continuation-in-part of application Ser. No. 09/149,098 filed Sep. 8, 1998, now abandoned claiming priority to provisional application Ser. No. 60/058,194 filed Sep. 8, 1997. This application also claims priority to provisional application Ser. Nos. 60/091,399 and 60/101,252 filed Jun. 30, 1998 and Sep. 21, 1998, respectively.

Acknowledgment of Government Funding

The invention was partially made with Government support under Grant No. HL 56819 awarded by the National Institutes of Health. The United States Government has certain rights in this invention.

FIELD OF THE INVENTION

The present invention relates generally to biocompatible materials. In particular, the present invention relates to cytomimetic systems having stabilized, phosphatidylcholine-containing polymeric surfaces. The biomaterials produced in accordance with the invention comprise various modular surface designs and have various applications such as in medical devices, vascular grafts, surgical equipment, drug delivery systems, etc.

BACKGROUND OF THE RELATED ART

The ability to repair, reconstruct and replace components of the human cardiovascular system is dependent upon the availability of blood compatible biomaterials. Biocompatibility refers to the interactions of living body tissues, compounds and fluids, including blood, etc., with any implanted or contacting polymeric material (biomaterial). Biocompatible biomaterials are of great importance in any biomedical application including, for example, in the implantation of vascular grafts and medical devices such as artificial organs, artificial heart valves, artificial joints, synthetic and intraocular lenses, electrodes, catheters and various other prosthetic devices into or on the body. Such applications, however, have been hampered by the lack of suitable synthetic materials that are stable when contacted with physiological fluids, particularly blood.

Exposure of synthetic biomaterials to body fluids such as blood, for example, can result in adverse reactions such as the formation of thrombi due to deposition of blood proteins (e.g., albumin, immunoglobulins, etc.) and/or adsorption of cell adhesive proteins (e.g., fibrinogen, fibronectin, vitronectin, etc.) causing platelet adhesion, activation and aggregation, as well as activation of the clotting cascade. Additionally, immune complexes can develop and stimulate undesirable immune responses such as proteolysis, cell lysis, opsonization, anaphylaxis, chemotaxis, etc.

Several approaches have been proposed for improving the biocompatibility of biomaterials useful in medical applications. For example, modifying the biomaterial surface to provide either low polarity or ionic charge or coating the surface with biological substances such as cells, proteins, enzymes, etc. has been used to prevent undesirable protein adhesion. Another approach involves the incorporation of an anticoagulant into the biomaterial, rendering the biomaterial antithrombogenic. A further approach involves the incorporation of various phospholipids into the biomaterial. An additional approach involves the binding of a heparin-quaternary amine complex, or other antithrombotic agent, to the biomaterial surface. However, many of these methods have the disadvantage of being nonpermanent systems in that the surface coating is eventually stripped off or leached away. For example, heparin, which is complexed to the biomaterial surface, is not only gradually lost from the polymer surface into the surrounding medium but also has limited bioactivity due to catabolism and its inherent instability under physiological conditions.

Thus, a need still exists for a biocompatible material for use in various medical applications possessing desired physical and surface characteristics and also exhibiting antithrombogenic properties.

One of the most intriguing developments in the past decade has been the recognition that membrane-mimetic systems having a phosphorylcholine component limit the induction of surface-associated blood clot formation. This biological property has been attributed to the large amount of surface bound water due to the zwitterion structure of the phosphorylcholine head group. It has also been suggested that specific plasma proteins which inhibit the blood clotting process are selectively adsorbed to this head group (Chapman [1993] Langmuir 9:39).

Natural membranes are utilized as models for the molecular engineering of membrane-mimetic biosystems because of the potential biological activities associated with natural membranes and their ability to self-organize as non-covalent aggregates. Phospholipids differing in chemical composition, saturation, and size have been utilized as building blocks in the design of structures of complex geometry, including lipid-based cylinders, cubes, and spheres. Surface-coupled bilayers have been produced by assembling a layer of closely packed hydrocarbon chains followed by exposure to either a dilute solution of emulsified lipids or unilamellar lipid vesicles (Spinke et al. [1992] Biophys. J. 63:1667; Florin et al. [1993] Biophys J. 64:375; Seifert et al. [1993] Biophys. J. 64:384). Langmuir-Blodgett techniques have also been used to construct supported bilayers via a process of controlled dipping of a substrate through an organic amphiphilic monolayer (Ulman [1991] *An Introduction to Ultrathin Organic Films from Langmuir-Blodgett to Self-Assembly*, New York: Academic Press). The overall significance of these design strategies lies in the ability to engineer surfaces in which the constituent members can be controlled, modified, and easily assembled with a high level of control over both order and chemistry. Of particular importance is the dialkyl moiety which facilitates the assembly of lipids with dissimilar head groups into surface structures of diverse biomolecular functionality and activity. Nonetheless, limited stability remains the major practical limitation of substrate supported membranes in which the constituent members are associated solely by non-covalent interactions.

In order to create robust surface structures, most membrane-mimetic systems for blood-contacting applications have been designed as copolymers containing the phosphorylcholine functional group in either side chains or, less frequently, the polymer backbone (Kojima et al. [1991] Biomaterials 12:121; Ueda, T. et al., [1992] Polym. J. 24:1259; Ishihara, K. et al. [1995] Biomaterials 16:873; Campbell et al. [1994] ASAIO J. 40(3):M853; Chen et al. [1996] J. Appl. Polym. Sci. 60:455; and Yamada et al. [1995] JMS Pure Appl. Chem. A32:1723). While these materials have improved stability and promising blood-contacting properties have been reported, a number of limitations exist. In particular, the ability to engineer surface properties on a molecular level, by taking advantage of the principal of self-organization intrinsic to amphiphilic molecules, is lost. In addition, the ability to early incorporate diverse biomolecular functional groups into the membrane-mimetic surface is also lost.

The present invention provides the synthesis of stabilized, phosphorylcholine-containing polymeric surfaces by first attaching or incorporating a self-assembled acryloyloxy-containing phospholipid monolayer on an alkylated substrate and then subjecting the unit to in situ polymerization. This invention contemplates the production of the biomaterial through a process of assembly on a supported monolayer of modular surface design units, each possessing the desired physicochemical surface properties. Specifically, an example is provided of a generated surface which exhibits improved in vivo blood biocompatibility in a primate animal model.

The present invention also provides a new biomimetic approach for generating an ultrathin organic barrier with the capacity for tailored transport and surface properties based upon a membrane-mimetic strategy. The extension of previous methodologies recently developed were utilized to produce a stable, lipid membrane-like bilayer on a hydrated alginate substrate. Marra, K. C.; Winger, T. M.; Hanson, S. R.; Chaikof, E. L.; *Macromolecules* 30, 6483 (1997). Marra, K. C.; Kiddani, D. D. A.; Chaikof, E.; *Langmuir* 13, 5697 (1997).

Transport characteristics and biocompatibility are critical membrane design properties for both the generation of controlled release drug delivery systems and capsules formulated as immunoisolation barriers for cell based therapy. Typically, membranes are produced with a variety of permeabilitites by phase inversion processes whereby polymer precipitation time, polymer-diluent compatibility, and diluent concentration influences membrane porosity. In other systems, barriers can be created by a polyelectrolyte coacervation reaction and molecular weight cutoff (MWCO) is modulated by osmotic conditions, diluents, and the molecular weight distribution of the polycationic species. The utilization of multicomponent polyanionic polymer blends and the diffusion time of oligocationic species through precast blends of polyanionic polymers have also been shown to be important variables in the control of MWCO. Alginate-calcium chloride systems represent a third approach for generating semipermeable capsules and have been used to produce monodisperse, spherical, transparent beads at a high production rate. As a cell-compatible polysaccharide, alginate is an appealing polymer and, in addition, facilitates cryopreservation of the encapsulated cell. Control of transport properties, however, requires post-coating with a poly(amino acid), typically, poly-L-lysine or a derivative thereof It is significant that transport characteristics are fundamentally governed, in all of these strategies, by the distribution of pore sizes created by thermodynamically driven physical processes.

Recent experiments have shown that non-covalently associated lipid bilayers can be deposited onto soft hydrated hydrophilic polymer cushions which in our view offers a route to barrier formation with enhanced control over both surface and transport properties. As described by Sackniann and coworkers (Kühner, M.; Tampè; Sackmann, E. Biophys J 67,217 (1994); Elender, G.; Kühner, M.; Sackmann, E. Biosensors Bioelectronics 11, 565 (1996)) a lipid monolayer is first formed on a dry dextran or polyacrylamide polymer film by vertical Langmuir-Blodgett dipping. The bilayer is completed after a second lipid layer is transferred using a Langmuir-Schaefer technique and the formulated film stored under water. In principle, functional reconstitution of membrane proteins including channels, transporters, and pores can be readily achieved. In addition, pores of well-defined size may be produced by suitable choice of template-forming guests in the membrane. The relatively low propensity towards biofouling is another appealing aspect of membrane-mimetic surfaces. As such, these systems have generated interest as a potential route to improved biocompatible biosensor design. Nonetheless, the stability of these supported membrane structures is limited since the lipid bilayer is not covalently coupled to the gel, nor are the self-associating lipid constituents stabilized in the two-dimensional plane by forces other than by van der Waal interactions.

SUMMARY OF THE INVENTION

The present invention provides a biocompatible biomaterial, comprising a phospholipid or phospholipid derivative comprising various functional groups (e.g., lipid, peptide, sugar, etc.) having specific chemical properties, which can function as a modular surface design unit to be incorporated or appended to a desired substrate on which it is then polymerized, thereby contributing new or specified biochemical characteristics to the polymerized and stabilized biomaterial. By first attaching a desired modular unit to a substrate (e.g., a polymer or a metal or derivatives thereof) and then carrying out in situ polymerization, the invention overcomes the disadvantages of unstable, non-permanent systems while providing the desired specificity of surface properties and biofunctionality in membrane-mimetic systems.

The present invention provides a biomaterial comprising a phospholipid or phospholipid derivative with a polymerizable monomeric group (e.g., acryloyloxy, methacryloyl, dienoyl, sorbyl, styryl, acrylamide, acrylonitrile, N-vinyl pyrrolidone, etc.). Such biomaterial phospholipid molecules form self-assembled monolayers that attach or absorb (e.g., through hydrophobic interactions, etc.) to a substrate whereon the polymerizable monomeric groups of the biomaterial phospholipid moieties are polymerized in situ. The biomaterial of the invention comprises two levels of attachment or cross reaction, i.e., (a) within the plane of phospholipid molecules, e.g., linking together of different phospholipid alkyl chains, and (b) between planes, e.g., interdigitating chains between phospholipid monolayers and the substrate surface.

Biomaterials taught in the art are often covalently linked to a substrate. In the instant invention, a biomaterial is provided that is non-covalently affixed to a substrate, permitting a detachment of the polymerized biomaterial from the substrate or a replacement of one type of polymerized biomaterial by another type of biomaterial of the invention. The instant invention also contemplates biomaterials that are covalently attached to a substrate to fulfill a specific purpose or to meet a specific environmental condition. The biomaterials of the invention serve as specific modular surface design units. This concept of biomaterials composed of modular design units offers increased variability, versatility and flexibility not only with respect to choice of functional groups on a molecular or microscopic level (e.g., in the phospholipid functional groups such as phosphorylalkylamino groups, etc.) but also in the assembly of units into a layer on a macroscopic surface structure.

The instant invention provides particular exemplification of biocompatible biomaterial surfaces that includes, but is not limited by, (a) in situ polymerized phospholipids on solid alkylated surfaces of a self-assembled monolayer, e.g., octadecyltrichlorosilane (OTS) on glass, (b) in situ polymerized phospholipids on a polymer supported monolayer of molecularly mobile alkyl chain, e.g, an amphiphilic, dialkyl-containing terpolymer bound to a gold-coated silicon wafer, and (c) in situ polymerized phospholipids onto hydrogel (e.g., alginate) surface transformed into a hydrophobic surface by addition of an amphiphilic copolymer.

It is a particular object of the invention to provide a biocompatible biomaterial surface modular unit comprising a phospholipid moiety comprising a polymerizable monomeric group, e.g., an acryloyloxy group, methacryloyl, dienoyl, sorbyl, styryl, acrylamide, acrylonitrile, N-vinyl pyrrolidone, etc., which unit is attached or adsorbed or affixed to an alkylated substrate, and polymerized thereon in situ, in an amount and orientation effective to provide an improved nonthrombogenic surface relative to a substrate without the polymerizable monomeric group containing phospholipid moiety attached thereto. The phospholipid moiety contains an alkyl amino group, e.g., a choline, ethanolamine or the like, and a phosphate polar group. In a preferred embodiment the biocompatible biomaterial has the structure (I):

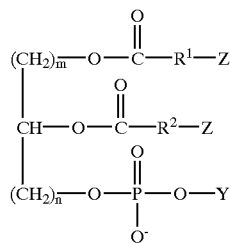

wherein $R^1$ is a $(C_1–C_{30})$alkyl group;
$R^2$ is a $(C_1–C_{30})$alkyl group;
m is 1–4;
n is 1–4;
Y is $—CH_2—CH_2—^+N(CH_3)_3$ or $—CH_2—CH_2—^+NH_3$

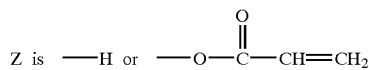

such that if $R^1$ is attached to Z=—H, then $R^2$ is attached to Z=

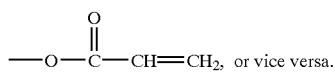

More preferably, the biocompatible biomaterial has the structure (I) wherein $R^1$ is a $(C_{12}–C_{30})$alkyl group; $R^2$ is a $(C_8–C_{14})$alkyl group; m is 1 and n is 1. In a preferred exemplification, the biocompatible material is 1-palmitoyl-2[12-(acryloyloxy)dodecanoyl]-sn-glycero-3-phosphorylcholine. The acrylate groups of the lipid molecules polymerize, forming a surface network in a two-dimensional plane.

The substrate of the invention includes, but is not limited to, an insoluble synthetic or natural, inorganic or organic material such as glass, silicon wafer, hydrogel (e.g., alginate, gelatin, collagen, polyhema, hydroxyethylmethacrylate, polyacrylamide, derivatives thereof, and the like) etc. The invention was particularly exemplified with alkylated substrates such as octadecyltrichlorosilane (OTS) coated glass, a self-assembling monolayer of an acylated octadecylmercaptan (e.g., ODT) on gold, octadecyl chains of an amphiphilic copolymer cast onto an alginate substrate, etc. A preferred substrate of the invention is exemplified by an amphiphilic dialkyl containing terpolymer bound to gold coated silicon wafers. Thus, a preferred biomaterial of the invention comprises an acryloyloxy-containing phospholipid which is adsorbed to an amphiphilic polymer surface (a molecularly mobile alkylated surface extending from a polymer bonded to a substrate) and which is polymerized thereon.

It is an additional object of the invention to provide a biocompatible biomaterial that exhibits enhanced stability. In a particular example of this embodiment, a stabilized, phosphatidylcholine-containing polymeric surface was produced by in situ polymerization of 1-palmitoyl-2-[12-(acryloyloxy)dodecanoyl-sn-glycero-3-phosphorylcholine at a solid-liquid surface. The phospholipid monomer was synthesized, prepared as unilamellar vesicles, and fused onto close-packed octadecyl chains as part of an amphiphilic terpolymer. Free-radical polymerization was carried out according to the method of the invention. Contact angle measurements demonstrated that the polymerized lipid monolayer when supported by the amphiphilic terpolymer exhibited enhanced stability than when supported on a self-assembled monolayer of octadecyl mercaptan (ODT)-coated surface.

It is another object of the invention to provide a medical device, e.g., a shunt, stent or graft, etc., comprising an alkylated substrate on which is attached and polymerized a biocompatible biomaterial modular unit comprising a phospholipid moiety comprising an alkylamino group (preferably choline) linked to a polar phosphate group and a polymerizable monomeric group (preferably an acryloyloxy group).

It is a further object of the invention to provide a method of preparing a biocompatible biomaterial having improved biocompatibility. This biomaterial must comprise a polymerizable monomer (preferably an acryloyloxy group)-containing phospholipid moiety (preferably a phosphatidylcholine moiety) attached to, and polymerized in situ on, a substrate in an effective amount and orientation such that an improved nonthrombogenic surface is obtained relative to the substrate without the acryloyloxy-containing phospholipid moiety. The method for preparing a biocompatible biomaterial of the invention comprises the steps of:

(a) synthesizing a phosphorylalkylamino-containing phospholipid comprising a polymerizable monomeric group;

(b) preparing lipid vesicles from said phospholipid of step (a);

(c) attaching or adsorbing said vesicles of step (b) onto a substrate; and (d) exposing the attached or adsorbed vesicles of step (c) to an initiator of polymerization such that the phospholipid undergoes in situ polymerization, forming a biopolymer or biomaterial having improved biocompatibility.

Improved biocompatibility is assessed according to the invention in a mammalian model in vivo or in an in vitro assay as a condition exhibiting decreased thrombogenicity or coagulation.

In further embodiments, the biomaterial of the invention is prepared to possess improved stability of a polymerized lipid monolayer at a solid-liquid interface. Improved stability is provided by utilizing a substrate comprising long chain acyl chains extending from an amphiphilic polymer surface.

In a particular embodiment, the invention was exemplified by in situ polymerized phospholipid on an amphiphilic, dialkyl-containing terpolymer.

In other embodiments, a stabilized, phosphatidylcholine-containing polymeric surface was produced by in situ polymerization of 1-palmitoyl-1-[12-(acryloyloxy)dodecanoyl]-sn-glycero-3-phosphoryl-choline at a solid-liquid interface. The phospholipid monomer was synthesized, prepared as unilamellar vesicles, and fused onto close-packed octadecyl chains as part of an amphiphilic copolymer. The copolymer was cast onto a hydrogel, e.g., alginate, thus transforming a hydrophilic surface into a hydrophobic surface. Free-radical polymerization of the phospholipid vesicles was carried out in aqueous solution. The supported monolayer displayed properties consistent with theoretical predictions for lipid membrane. The present invention provides a method for the transformation of a hydrophobic surface into a hydrophilic antithrombogenic surface.

In various exemplifications of the invention, free-radical polymerizations were carried out using a water-soluble initiator, e.g., 2,2'-azobis(2-methylpropionamidine) dihydrochloride (AAPD), or an oil-soluble initiator, e.g., 2,2'-azobisisobutyronitrile (AIBN).

It is yet another object of the invention to provide a biopolymer or biomaterial, prepared by the method of the invention, that demonstrates acceptable stability under static conditions in water and air, as well as in the presence of a high shear flow environment. In addition, this biopolymer or biomaterial, prepared by the method of the invention, exhibits blood compatibility in a mammalian model system. In a particular embodiment of the invention, an arteriovenous shunt prepared with a biomaterial of the invention, when placed in a baboon, revealed minimal platelet deposition.

DETAILED DESCRIPTION OF THE INVENTION

Figure 1:
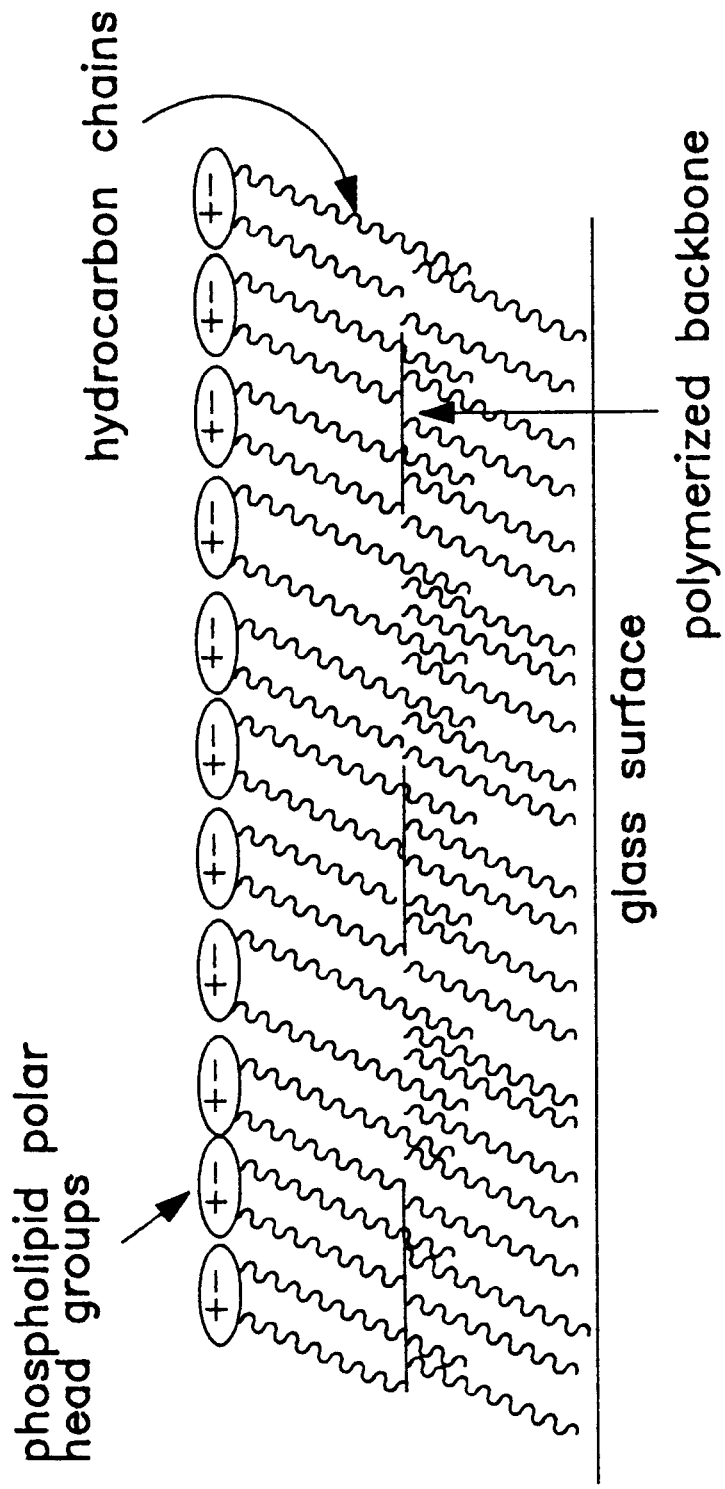
FIG. 1 illustrates schematically the structure of a polymerized phospholipid surface on a glass.

The following definitions are provided to remove any potential ambiguities as to the intent or scope of their usage in the specification and claims.

The term biocompatible or biocompatibility as used herein refers to the quality of interaction between an implanted or contacting polymeric material or biomaterial and a living body tissue, compound or fluid, e.g., blood, etc.

The term improved biocompatibility as used herein refers to the condition of a test biomaterial wherein the test biomaterial shows reduced platelet adhesion or spreading or the like upon interaction with blood or blood fractions than when compared to a control biomaterial. The term improved biocompatibility denotes decreased thrombogenicity or coagulation when compared to a control.

The term improved stability as used herein refers to the stability of a lipid monolayer at a liquid-solid interface as determined by the absence of significant increases in serial contact angle measurements of surface properties, as is commonly used in the art. An increase in water contact angles over time was correlated with decreased stability.

The term substrate as used herein refers to any synthetic or natural material that is insoluble in physiological fluids, for example, metal (e.g., titanium, stainless steel, etc.), glass (e.g., soda glass, silica glass, etc.), inorganic material or organic material (e.g., hydrogel, alginate, gelatin, collagen, polyacrylamide, methacrylate, etc). The instant invention contemplates that the phospholipid units of the invention are attached or adsorbed to substrates or, alternatively, that substrates can be modified appropriately (e.g., addition of polymerizable groups, e.g., acrylate groups, to the terminal end of surface alkyl chains) for covalent attachment of the phospholipid unit to the substrate.

The term phosphorylcholine as used herein refers to a molecule having the structure $(CH_3)_3N^+-CH_2-CH_2-O-PO_3^{2-}$.

The termphosphatidlcholine as used herein refers to a molecule having the structure:

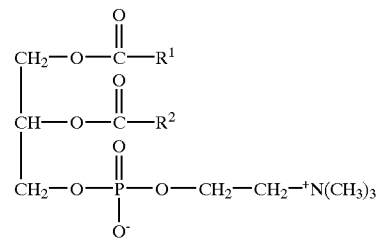

wherein $R^1$ and $R^2$ are usually long chain fatty acyl groups.

The term effective amount and orientation as used herein refers to the amount of phospholipid per substrate as well as the orientation of the phospholipid with respect to the substrate that is required to produce a biomaterial of the invention that exhibits improved biocompatibility.

The biocompatibility of biomaterials that are in contact with blood or blood fractions, for example, in various medical applications, is improved by the presence of a phospholipid moiety. By attaching a phospholipid moiety to a substrate, the extent and severity of adverse reactions between the substrate and the blood is reduced.

Phospholipid derivatized surfaces have been prepared by focusing on the synthesis of a variety of copolymers containing the phosphorylcholine (PC) functional group in either side chains or the polymer backbone (Kojima et al. [1991] Biomaterials 12:121; Ueda et al. [1992] Polymer. J. 24:1259; Ishihara et al. [1995] Biomaterials 16:873; Campbell et al. [1994] ASAIO Journal 40:M853; and Chen et al. [1996] J. Appl. Polym. Sci. 60:455). For example, a copolymer of MPC (2-methacryloyloxyethyl-phosphorylcholine) and styrene was prepared by Kojima et al. (1991) supra and the MPC so obtained was further polymerized with various alkyl methacrylates (e.g., butylco-n-methacrylate (BMA) (Ueda et al. [1992] supra). In copolymers such as BMA, hysteresis values averaged 80°, which was attributed to both surface roughness and the rearrangement of hydrophilic phosphorylcholine head groups on contact with water. Significantly, blood compatibility decreased as the length of the alkyl chain increased.

Other phosphorylcholine-containing biomaterials included (a) a copolymer of MPC, BMA (n-butyl-methacrylate) and a methacrylate with a urethane bond in the side chain, which was cast onto a segmented polyurethane (Ishihara et al. [1995] supra) and (b) a copolymer of MPC and lauryl methacrylate, which was coated onto metal, glass and other polymer surfaces (Campbell et al. [1994] supra). Recently, a polymer was synthesized to comprise PC groups in the main backbone chain (Chen et al. [1996] J. Appl. Polym. Sci. 60:455; Yamada et al. [1995] JMS Pure Appl. Chem. A32:1723) and due to the presence of docosyl or stearyl side chains, this polymer self-organizes. In all cases, coating stability was attributed to multipoint adsorption of the alkyl chains to the underlying surface.

Although the literature concerning two-dimensional polymerization of lipids in the form of vesicles is extensive, there are few studies which have evaluated the feasibility of in situ polymerization of dialkyl amphiphiles at a solid-liquid surface. The polymerization of bis-methacrylate and bis-diacetylene containing phospholipids onto polyethylene was reported in Regen et al. (1983) Macromolecules 16:335. However, the polymerization of a monoacrylate-lipid monomer was unsuccessful. Further, cross-linked lipid networks on a solid surface have been produced by polymerization of bis-diacetylene containing phospholipid after Langmuir-Blodgett deposition (McLean et al. [1983] Thin Solid Films 99:127 and Regen et al. [1983] Macromolecules 16:335). In this system, polymerization proceeds most rapidly when the crystalline phase of the polymer most closely resembles that of the monomer. Preservation of the structural order displayed by the monomeric lattice is required. Consequently, a high degree of surface defects are common in crosslinked diacetylene monolayers. In none of these prior systems were phospholipids adsorbed onto alkylated surfaces. Further, biocompatibility was not characterized nor was stability defined.

Despite more than four decades of research, a clinically durable blood compatible surface remains an elusive goal. In this regard, the biological membrane appears to be an ideal starting point for the generation of a synthetic blood-compatible substrate. The present invention provides a method of in situ polymerization of a monoacrylate phospholipid as a convenient means of stabilizing at a solid-liquid interface a monolayer having desired blood contacting properties. The supported monolayers of the invention displayed physicochemical characteristics consistent with theoretical predictions of a lipid membrane. In a particular embodiment, the invention was exemplified by the polymerization of a monomeric phospholipid, e.g., 1-palmitoyl-2-[12-(acryloyloxy)dodecanoyl]-sn-glycero-3-phosphorylcholine, at a solid-liquid interface on alkylated glass. In another embodiment of the invention, this monoacrylate phospholipid was polymerized in situ on a molecularly mobile alkylated surface bonded to a gold-coated silicon wafer. In yet another embodiment of the invention, a monoacrylate phospholipid was fused onto close-packed acyl chains as part of an anphiphilic copolymer which was then cast onto a hydrogel (alginate) substrate.

Figure 2:
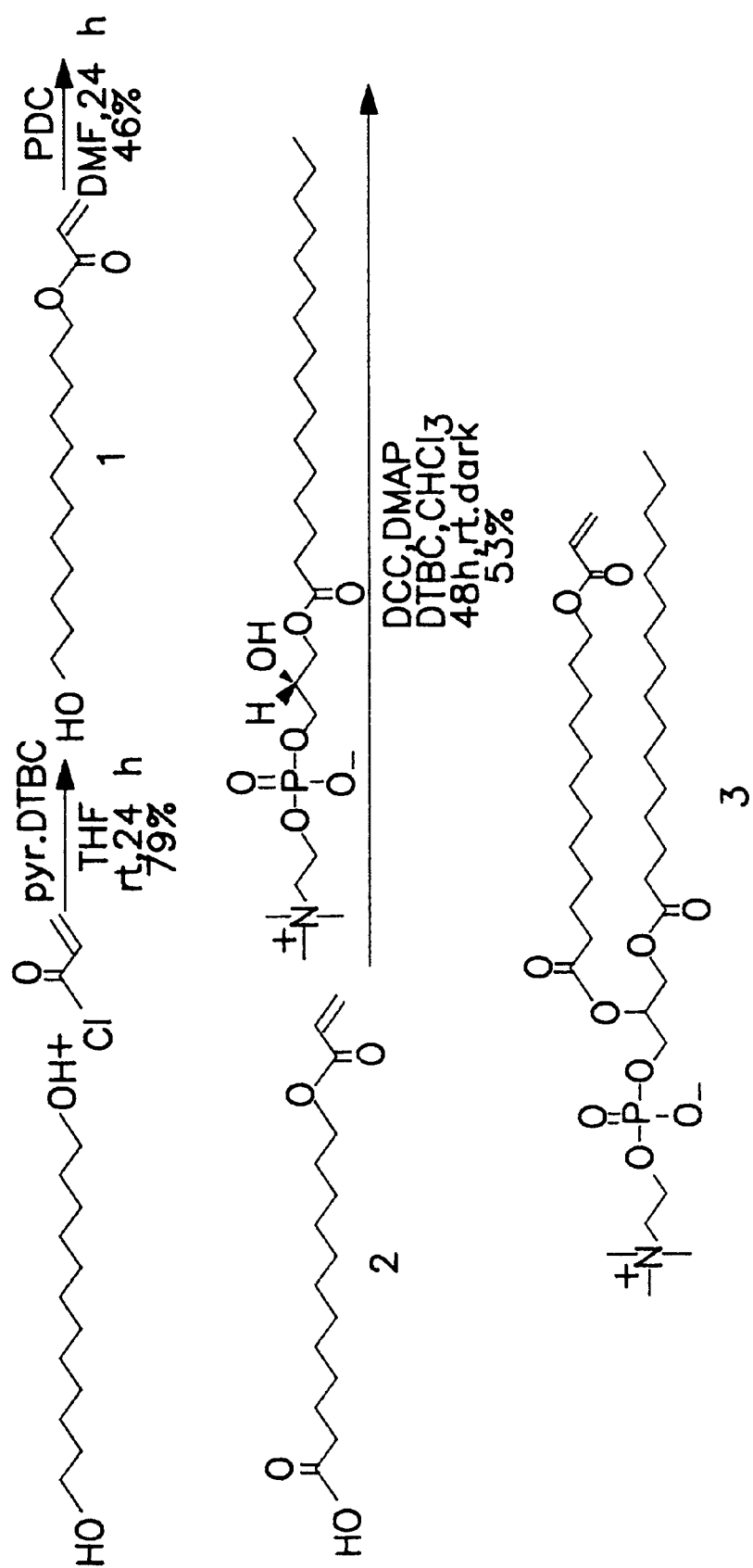
FIG. 2 is a scheme illustrating the preparation of a phospholipid monomer.

A stabilized phospholipid monolayer surface (FIG. 1) was prepared using a strategy based upon the fusion of unilamellar vesicles with an alltylated substrate followed by in situ polymerization. Briefly, established general methodologies were utilized for the synthesis of the phospholipid monomer (FIG. 2) (Sells et al. [1994] Macromolecules 27:226), preparation of liposomes, and fusion of the native lipid vesicles onto alkylated surfaces (Plant [1993] Langmuir 9:2764). Optimized octadecyltrichlorosilane (OTS) coated substrates, characterized by goniometric measurements and AFM, displayed advancing water contact angles of 110–113° and were topographically uniform with an average roughness of less than 2 Å over 1 $\mu m^2$. In order to facilitate vesicle/surface fusion, experiments were performed at 40° C., above the known $T_m$ for the acrylate functionalized lipid monomer (Lamparski et al. [1993] J. Am. Chem. Soc. 115:8096). After fusion, either a water-soluble free radical initiator, AAPD, or an oil soluble initiator, AIBN, was added directly to the film in the buffer solution and polymerization was initiated by heat (65–70° C.) (see FIG. 3). The polymerized film was rinsed copiously with water, and surface characterization performed.

Several parameters were investigated in optimizing vesicle fusion and polymerization schemes including: vesicle size and concentration, fusion time, monomer/initiator concentration ratio, and type of initiator. In the process, it was postulated that a uniform lipid monolayer would be associated with a lower water contact angle than one associated with surface defects. While three different vesicles sizes were initially utilized, 200, 600 and 2000 nm, the effectiveness of surface fusion was unaffected by this parameter and all subsequent studies were performed with 600 nm vesicles. Likewise, monomer fusion to the alkylated substrate was examined as a function of vesicle concentration (750–1500 $\mu M$) and fusion time (24–48 hours). Contact angles were unaffected by these parameters, and all ensuing studies were performed at a concentration of 1200 $\mu M$ and a fusion time of 24 hours. As anticipated, larger ratios of monomer to initiator lead to lower contact angles, presumably related to a higher degree of polymerization, and a monomer:initiator ratio of 10:1 was selected on the basis of these investigations.

Further, the effectiveness of two free radical initiators was studied: AAPD and AIBN, which are soluble in water and organic solvents, respectively. It was expected that AAPD, as a water soluble initiator, would be more efficient since polymerization was carried out at a solid-aqueous interface. In addition, AAPD has also been shown to penetrate the hydrophobic layer above the $T_m$ of the polymerizable phospholipids (Ohno et al. [1987] J. Polym. Sci.: Part A: Polym. chem. 25:2737). Although successful polymerization was obtained by pre-sonication of AIBN into vesicles, lower contact angles were observed in the AAPD-initiated system. Table 1 displays the contact angles for the optimized system.

TABLE 1

Final Polymer: Polymerization Conditions and Contact Angles.

| Polymer Run[a] | Advancing Contact Angle (°) | Receding Contact Angle (°) | Hysteresis (° C.) |
| --- | --- | --- | --- |
| 1 | 63.6 ± 5.3 | 45.4 ± 2.7 | 18.2 |
| 2 | 63.3 ± 6.3 | 47.3 ± 6.9 | 16.0 |
| 3 | 64.8 ± 1.5 | 45.0 ± 2.8 | 19.8 |
| 4 | 65.2 ± 1.6 | 46.8 ± 2.5 | 18.4 |
| 5 | 64.6 ± 3.6 | 43.8 ± 4.3 | 20.8 |
| 6 | 62.4 ± 3.4 | 44.4 ± 5.1 | 18.0 |
| Alkylated Glass (OTS) | 111.2 ± 2.4 | 105.0 ± 1.4 | 6.2 |

[a]Polymerization conditions: initiator was AAPD; vesicle size was 600 nm; concentration was 1200 $\mu M$; fusion time was 24—48 hours at 40° C.

Average advancing and receding water contact angles of 64° and 44°, respectively, were observed. As such, the hydrophilicity of the film was confirmed, particularly when compared to the base OTS substrate which exhibited an average contact angle of 111°. In addition, an average hysteresis 18° was noted. Hysteresis, defined as the difference between advancing and receding contact angles, is indicative of kinetic and thermodynamic film properties. For example, surface roughness and chemical heterogeneity, either intrinsically or due to molecular reorientation after penetration of water into the polymer film, may lead to large hysteresis values. In this regard, it bears reemphasis that advancing and receding angles measure the contact of water and dry and pre-wetted surfaces, respectively. Thus, hysteresis values in our polymer system represent, at least in part, the reorientation of hydrophilic phosphorylcholine moieties in order to minimize the free energy at the solid-water interface.

Angle-dependent ESCA measurements were carried out to further define atomic level surface properties (Tables 2 and 3). Assuming 2.5 OTS chains per phospholipid unit, theoretical atomic percent surface concentrations were calculated. In this system, P and N were identified, providing additional confirmation of a polymerized lipid film. Moreover, observed atomic percent concentrations, particularly C and O, were consistent with predictions for close-packed monolayer formation with near-normal alignment of lipid chains. Overall, ESCA has been used infrequently in the characterization of PC based surfaces and no angle-dependent data reported to date. However, these results are consistent with those of Hayward et al. (1986) Biomaterials 7:252 and Köhler et al. (1996) J. Biomed. Mat. Res. 32:237 of PC derivatized glass.

TABLE 2

ESCA Results for Polymer.

| Polymer | Take-Off Angle | | | Approximate Theoretical % |
|---|---|---|---|---|
| | 15° | 45° | 90° | |
| C | 78.8 ± 0.7 | 69.2 ± 4.9 | 65.6 ± 6.3 | 79.3 |
| P | 0.7 ± 0.2 | 0.6 ± 0.3 | 0.8 ± 0.4 | 0.9 |
| O | 16.3 ± 0.8 | 22.2 ± 3.8 | 24.2 ± 4.3 | 16.5 |
| N | 0.4 ± 0.1 | 0.6 ± 0.1 | 0.6 ± 0.4 | 0.9 |
| Si | 3.8 ± 0.6 | 7.4 ± 1.1 | 8.8 ± 1.3 | 2.4 |

TABLE 3

ESCA Results for OTS Glass.

| OTS | Take-off Angle | | | Theoretical % |
|---|---|---|---|---|
| | 15° | 45° | 90° | |
| C | 85.3 ± 1.7 | 62.6 ± 0.5 | 53.2 ± 0.4 | 81.8 |
| Si | 4.6 ± 0.8 | 12.5 ± 0.3 | 14.3 ± 1.0 | 4.6 |
| O | 10.0 ± 1.0 | 24.7 ± 0.4 | 32.5 ± 0.7 | 13.6 |

Non-polymerized substrate-supported phospholipid membranes are unstable on transfer from water to air, even for brief surface measurements (Solletti et al. [1996] Langmuir 12:5379). Thus, following polymerization, serial contact angles were determined in order to characterize the stability profile of the lipid monolayer (Table 4).

TABLE 4

Static Stability Contact Angles for the Optimal Polymer (Adv./Rec.)

| Polymer | Initial (°) | One Day (°) | Two Days (°) | One Week (°) |
|---|---|---|---|---|
| 1 | 65/44 (±4) | 75/56 (±2) | 77/55 (±5) | 81/55 (±4) |
| 2 | 65/45 (±3) | 78/59 (±5) | 76/56 (±4) | 78/56 (±2) |

The largest increase in contact angle was noted within the first 24 hours, likely due to the leaching of non-polymerized lipid monomer, and remained relatively unchanged for at least two weeks thereafter. Under operating conditions, blood contacting surfaces are usually subjected to wall shear rates of 20 dyn/cm$^2$ or less. As a short term test, films were exposed to a shear force of 200 dyn/cm$^2$ at 37° C. for either 10 or 60 minutes (Table 5). Similarly, the largest change in the contact angle was noted early in the exposure period.

TABLE 5

Shear Flow Contact Angle Results.

| Polymer | Advancing Contact Angle (°) | Receding Contact Angle (°) | Hysteresis (°) |
|---|---|---|---|
| Initial | 71.7 ± 2.9 | 50.3 ± 7.7 | 21.4 |
| 10 minutes | 76.8 ± 0.6 | 60.3 ± 0.2 | 16.5 |
| 60 minutes | 84.5 ± 6.0 | 58.0 ± 5.0 | 33.5 |

Figure 4:
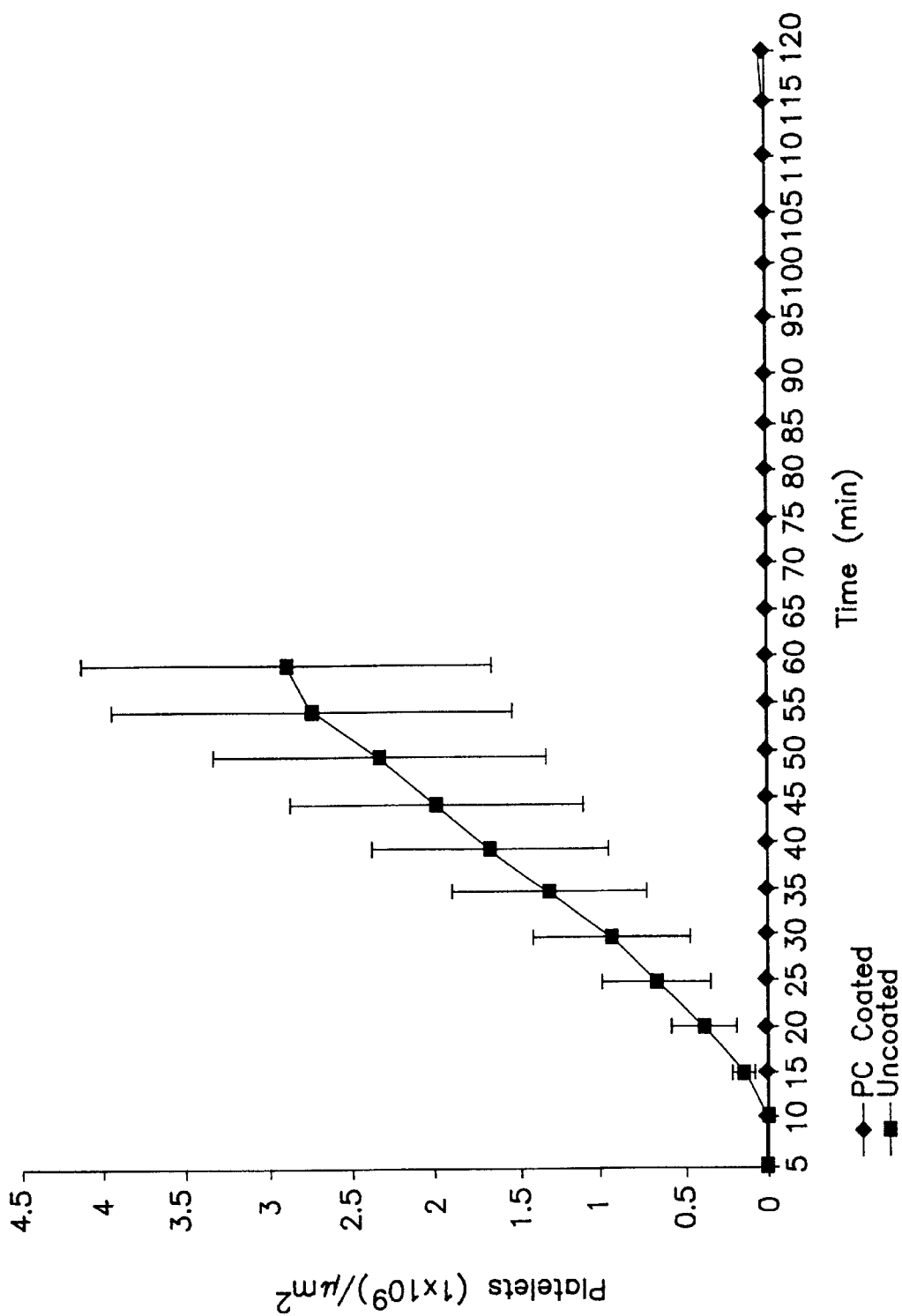
FIG. 4 illustrates platelet deposition on test surfaces in a baboon femoral arteriovenous shunt. Series 1 and 2 represent untreated glass and phospholipid coated surfaces, respectively. Data is presented as mean±standard error of three separate samples.

Short-term blood contacting studies are used in the art to predict the risk of surface-induced clot formation. Such tests provide a convenient mechanism for screening the clinical performance of a biomaterial. In particular, the baboon is the animal of choice for blood compatibility testing since its blood clotting system most closely resembles that of man (Feingold et al. [1986] Am. J. Vet. Res. 47:2197). Throughout a two hour time period, minimal platelet deposition was observed on polymerized phospholipid surfaces, in contrast to the high level of reactivity exhibited by uncoated glass surfaces (FIG. 4).

Figure 3:
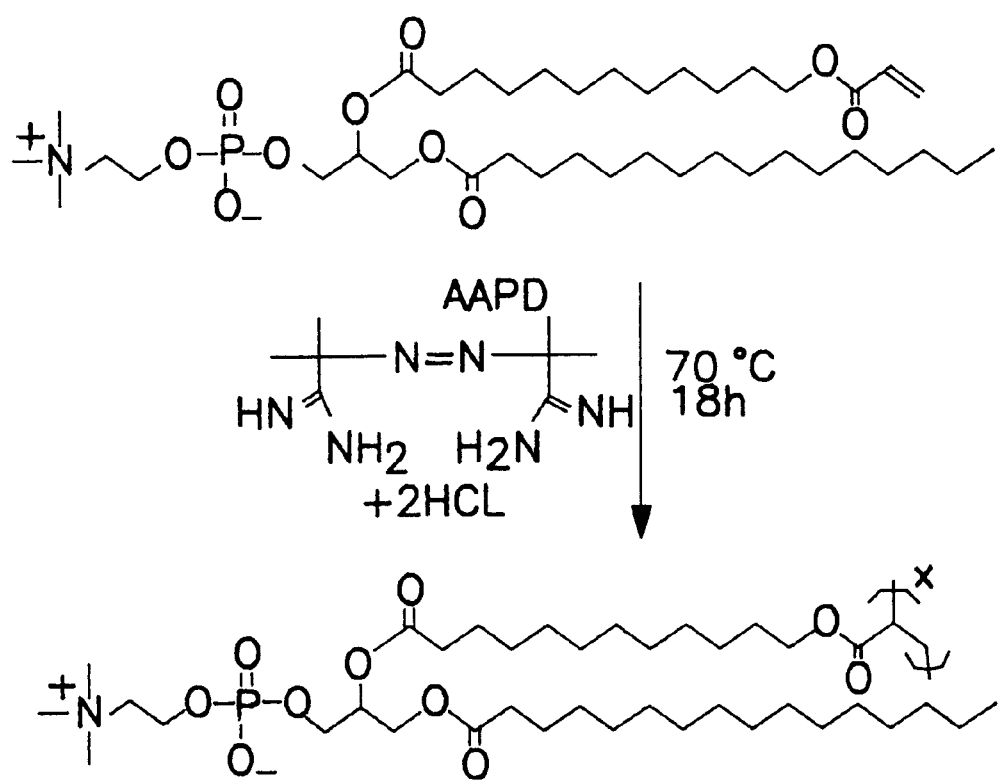
FIG. 3 is a scheme illustrating the polymerization of phospholipid.
Figure 5:
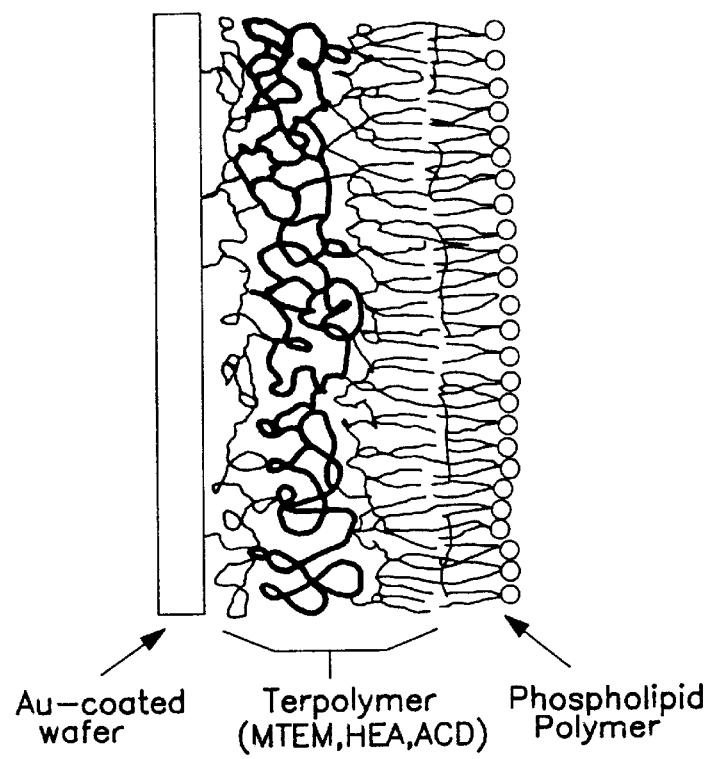
FIG. 5 is a schematic of polymerized phospholipid on a terpolymer surface.

In a different embodiment of the invention, the postulate was investigated that vesicle fusion and in situ polymerization would proceed more efficiently on a molecularly mobile alkylate substrate surface. A phospholipid monomer of the invention was prepared by the esterification of 12-(acryloyloxy)-1-dodecanoic acid with 1-palritoyl-2-hydroxy-sn-glycero-3-phosphocholine. A molecularly mobile alkylated surface was prepared by binding a sulfur-containing terpolymer to a gold-coated silicon wafer. The phospholipid was fused to and polymerized on the terpolymer (FIG. 5). The polymerization of the phospholipid was carried out in aqueous solution at 70° C. utilizing a water-soluble, free radical initiator (FIG. 3).

Figure 6:
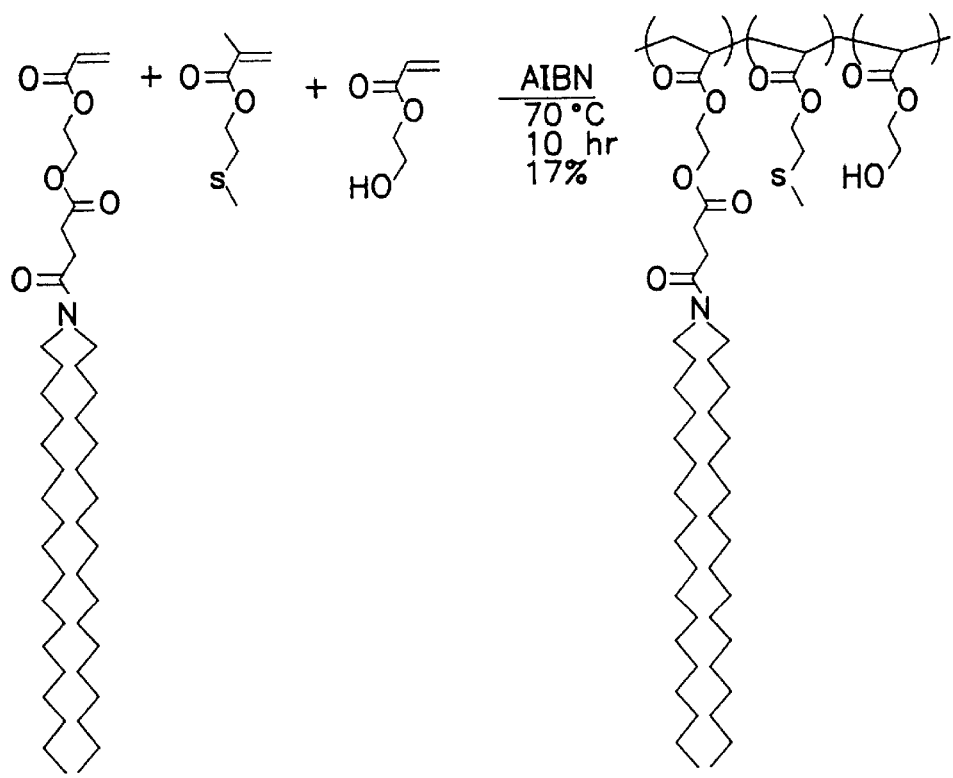
FIG. 6 is a scheme illustrating the preparation of a terpolymer.
Figure 7:
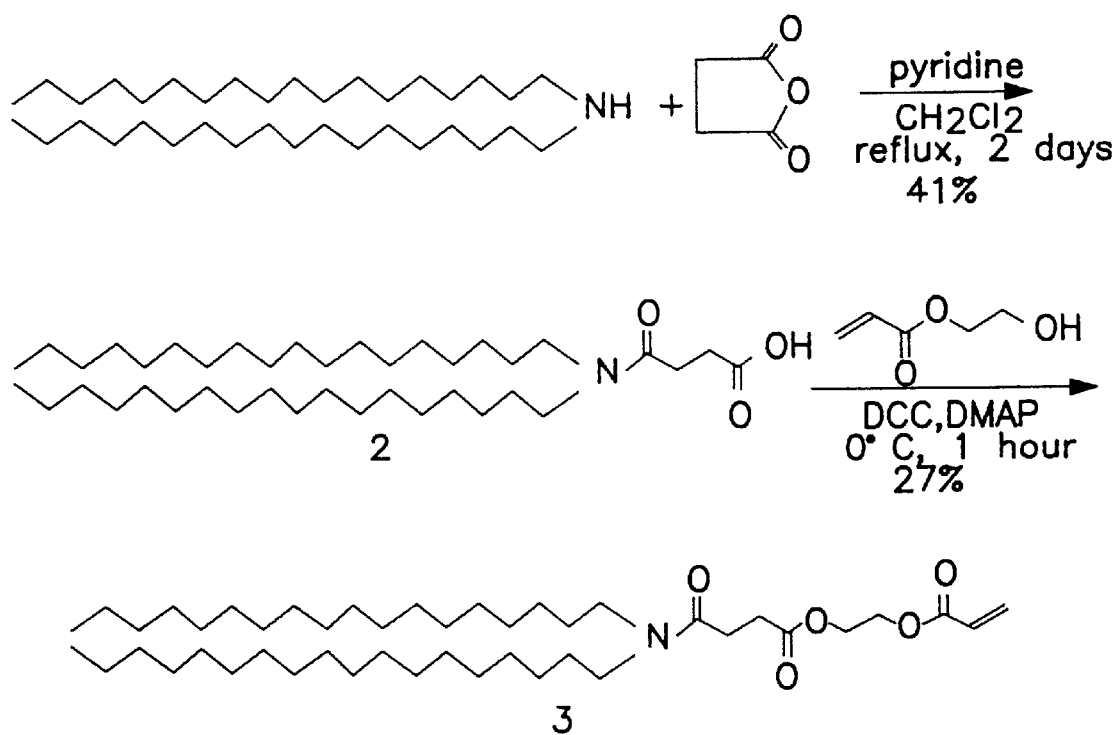
FIG. 7 is a scheme illustrating the preparation of a hydrophobic monomer.

The terpolymer consists of two commercially available monomers, 2-hydroxyethyl acrylate (HEA) and 2-(methylthio)ethyl methacrylate (MTEM), and a third monomer, AOD, that was synthesized in accordance with FIG. 6. The statistical composition of the terpolymer is 6:3:1, HEA:AOD:MTEM. This polymer was obtained by an AIBN-initiated free radical polymerization (FIG. 7). The sulfur-containing methacrylate monomer binds to gold as an anchor, whereas the hydrophobic monomer AOD migrates to the surface, exposing an ordered layer of alkyl chains for vesicle fusion. The hydrophilic HEA component acts as a "cushion" which facilitates the self-assembly of the alkylated chains at the solid-aqueous interface. Fusion of the lipid vesicles was executed following established methods (e.g., Plant [1993] Langmuir 9:2764; Lamparski et al. [1993]

J. Am. Chem. Soc. 115:8096, etc.). In order to facilitate vesicle/surface fusion, experiments were performed at 40° C., above the known $T_m$ for the acrylate functionalized lipid monomer (Bain [1989] Ph.D. Thesis, Harvard University). After fusion, a water-soluble free radical initiator, AAPD, was added directly to the film in the buffer solution and polymerization was initiated by heat (65–70° C.). The polymerized film was rinsed copiously with water, and surface characterization was performed.

The optimized polymerization parameters included a vesicle size of approximately 600 nm, vesicle concentration of approximately 1200 $\mu$M, a fusion time of approximately 24 hours, a monomer:initiator ratio of approximately 10:1, and a polymerization time of approximately overnight at 70° C. Initial characterization of optimized surfaces was performed using contact angle goniometry (Table 6).

TABLE 6

Static Stability Contact Angles for All Polymers (°) (Adv./Rec.).

| Polymer Substrate | Prior to fusion | Initial[a] | One Day | One Week |
|---|---|---|---|---|
| OTS | 111/105 (±2) | 65/45 (±4) | 77/58 (±5) | 80/56 (±4) |
| ODT | 107/104 (±2) | 76/58 (±6) | 84/64 (±6) | 88/71 (±5) |
| Terpolymer | 102/82 (±3) | 58/31 (±5) | 64/36 (±5) | 68/40 (±5) |

[a]Contact angles were taken immediately after fusion and subsequent polymerization of phospholipid monomer.

Also included in Table 6 are the contact angles of the alkylated substrates. The base substrates are hydrophobic, while the resulting phospholipid polymeric surfaces are hydrophilic. Average advancing and receding water contact angles of 58° and 31°, respectively, were observed for the polymer fused onto the terpolymer. As indicated above, advancing and receding water contact angles of 64° and 44°, respectively, were obtained for this phospholipid polymer supported on an OTS/glass substrate.

In other embodiments of the invention, ODT on Au was utilized as a substrate for fusion and polymerized. Under these conditions, advancing and receding water contact angles of 76° and 58°, respectively, were observed (Table 6). Ellipsometry measurements were taken of the substrates as well as the phosphorylcholine (PC)-polymers (Table 7).

TABLE 7

Ellipsometry Results (Å).

| Sample | Initial Thickness | Thickness after 24 Hours H$_2$O Immersion | Thickness after 24 Hours Vacuum Drying |
|---|---|---|---|
| Terpolymer substrate | 45.9 ± 3.5 | 73.1 ± 5.3 | 50.7 ± 8.5 |
| Polymer/Terpolymer | 144.7 ± 23.2 | 166.5 ± 13.2 | 135.6 ± 3.2 |

Film thickness for the ODT/Au substrate was found to be 18.1±0.3 Å, as expected, indicating a close-packed, self-assembled monolayer of octadecyl chains (Bain [1989] supra). The film thickness for the PC-polymer on the ODT/Au substrate is 65.5±15.0 Å, which is comparable to the theoretical thickness. The results for the terpolymer substrate are also as expected. However, when the terpolymer substrate was stored in water for 24 hours, the film thickness increased (Table 7). This may indicate an absorption of water by the terpolymer, most likely by the HEA segment. This may also reveal an expansion of the HEA segment in water. This approximately 30 Å expansion is also seen with the PC-polymer on the terpolymer substrate (Table 7). A PC-polymer on the terpolymer was dried under vacuum for 24 hours to remove any traces of water. Ellipsometry measurements were then taken, and the film thickness decreased by approximately 30 Å after the vacuum drying. However, film thickness remains greater than expected. A plausible explanation may be the refractive index value assumed for the system. Since this is a novel system and no refractive indices are reported in the literature, a typical value of 1.4500 was utilized. Another possibility is that the phospholipid is forming multilayers on the surface. If that were the case, ESCA results could indicate an excess of phosphorus. However, as described below, that is not the case.

Angle-dependent ESCA measurements were carried out to further define atomic level surface properties (Tables 8–11). Three angles were utilized (15°, 45° and 90°). The theoretical compositions were determined by atom counting.

TABLE 8

ESCA Results for ODT/Au Substrate.

| ODT | Take-off Angle | | | Theoretical % |
|---|---|---|---|---|
| | 15° | 45° | 90° | |
| C | 91.9 ± 1.0 | 73.9 ± 1.7 | 63.2 ± 0.9 | 87.1 |
| S | 2.1 ± 1.3 | 2.3 ± 0.2 | 2.5 ± 0.9 | 12.9 |
| Au | 6.0 ± 2.1 | 23.9 ± 1.9 | 34.2 ± 0.2 | — |

The results for the ODT substrate are given in Table 8 and are as expected (Bain [1989] supra). The results for the PC-polymer on ODT/Au are given in Table 9 (assuming 2.5 OTS chains per phospholipid unit).

TABLE 9

ESCA Results for PC-Polymer on ODT/Au.

| | Take-off Angle | | | Theoretical % |
|---|---|---|---|---|
| | 15° | 45° | 90° | |
| C | 71.8 ± 7.1 | 65.1 ± 5.0 | 63.5 ± 8.4 | 77.9 |
| O | 18.7 ± 0.9 | 12.9 ± 7.0 | 13.6 ± 7.3 | 12.4 |
| N | 1.2 ± 0.2 | 0.9 ± 0.6 | 1.6 ± 0.5 | 1.1 |
| P | 0.9 ± 0.4 | 1.0 ± 0.3 | 1.0 ± 0.9 | 2.4 |
| S | 2.4 ± 2.1 | 3.4 ± 1.3 | 2.9 ± 1.7 | 6.2 |
| Au | 1.7 ± 0.6 | 11.4 ± 7.6 | 13.1 ± 13.6 | — |

The results, especially at the topmost surface (15°), with very little gold detected, are near theoretical predictions. The results for the terpolymer/Au substrate are given in Table 10.

TABLE 10

ESCA Results for Terpolymer/Au Substrate.

| | Take-off Angle | | | Theoretical % |
|---|---|---|---|---|
| | 15° | 45° | 90° | |
| C | 71.7 ± 7.7 | 72.5 ± 1.5 | 68.8 ± 7.5 | 76.6 |
| O | 19.5 ± 2.2 | 16.2 ± 0.4 | 17.1 ± 3.9 | 18.2 |
| N | 1.4 ± 0.6 | 1.3 ± 0.1 | 2.2 ± 1.2 | 1.6 |
| S | 1.0 ± 0.6 | 1.2 ± 0.5 | 1.1 ± 0.6 | 3.6 |
| Au | 6.1 ± 8.3 | 8.8 ± 0.5 | 10.7 ± 8.8 | — |

Again, at the shallowest depth (15°) the atomic percentages approximate theoretical predictions. Assuming 2.5 OTS chains per phospholipid unit, the atomic percent surface concentrations were calculated for the PC-polymer on terpolymer/Au substrate (Table 11).

TABLE 11

ESCA Results for PC-Polymer on Terpolymer/Au.

| | Take-off Angle | | | |
|---|---|---|---|---|
| | 15° | 45° | 90° | Theoretical % |
| C | 73.6 ± 4.2 | 73.0 ± 1.3 | 70.5 ± 1.3 | 73.5 |
| O | 21.9 ± 1.9 | 20.9 ± 1.6 | 21.8 ± 1.6 | 20.6 |
| N | 1.3 ± 0.1 | 1.8 ± 0.6 | 2.2 ± 0.7 | 1.8 |
| P | 1.1 ± 0.9 | 1.2 ± 0.3 | 1.0 ± 0.3 | 2.0 |
| S | 0.8 ± 0.2 | 0.8 ± 0.4 | 0.6 ± 0.1 | 2.1 |
| Au | 0.2 ± 0.2 | 1.5 ± 1.0 | 2.9 ± 1.7 | — |

Phosphorus and nitrogen were identified, providing additional confirmation of a polymerized lipid film. There is considerably less gold detected in the PC-terpolymer system, confirming that this is a thicker film as determined by ellipsometry. Overall, ESCA has been used infrequently in the characterization of PC based surfaces. However, the results are consistent with those of Hayward et al. (1986) Biomaterials 7:252 and Köhler et al. (1996) J. Biomed. Mat. Res. 32:237, for PC derivatized glass.

Short-term water stability tests were executed and the results for the three substrates are given in Table 6 Water contact angles were measured intermittently by removing the polymer films from their water storage, air-drying, and measuring contact angles. After one week, the phospholipid polymer on the terpolymer substrate remains hydrophilic, indicating a stable PC surface. Differences in substrates leads to a noticeable difference in contact angles with the terpolymer providing the lowest water contact angles. The terpolymer may provide a more flexible surface and this could enhance fusion or more efficient polymerization. Conversely, the OTS/glass and ODT/gold substrates are more rigid and may lead to less effective vesicle fusion. A molecularly mobile alkylated surface provides a better support for the creation of polymerized lipid film.

The binding of a sulfur-containing polymer to a gold substrate was reported previously by Spinke et al. who reported the fusion of phospholipid vesicles onto a multi-functional amphiphilic terpolymer bound to gold. The polymers were composed of HEA, a disulfide-containing methacrylate, and a hydrophobic methacrylate containing octadecyl side chains. Recently, Sun et al. ([1993] Langmuir 9:3200) investigated the film properties of terpolymers containing HEA as well as a disulfide-containing acrylate and methoxyethyl acrylate bound to gold. ESCA results indicated an exposed acrylate backbone and water contact angles were 45–68°. Ellipsomerty results, however, were not as expected which was attributed to inherent errors associated with assumed refractive index values. In a subsequent report, Sun et al. ([1994] J. Vac. Sci. Technol. 12:2499) observed that the average film thicknesses varied as a function of the density of the anchoring dithioalkyl chains. Presumably,more backbone loops and longer segments in the HEA segments lead to a larger hydrophilic "cushion" and consequently greater thickness values. Most recently, disulfide-containing, siloxane terpolymers were prepared (Sun et al. [1996] J. Am. Chem. Soc. 118:1856). One siloxane segment contained fluorocarbon side chains. The terpolymer was shown to bind to gold and phase segregate to obtain a low energy surface. Contact angle and ESCA results confirmed a fluorocarbon surface and ellipsometry revealed a film thickness of approximately 30 Å.

Figure 8:
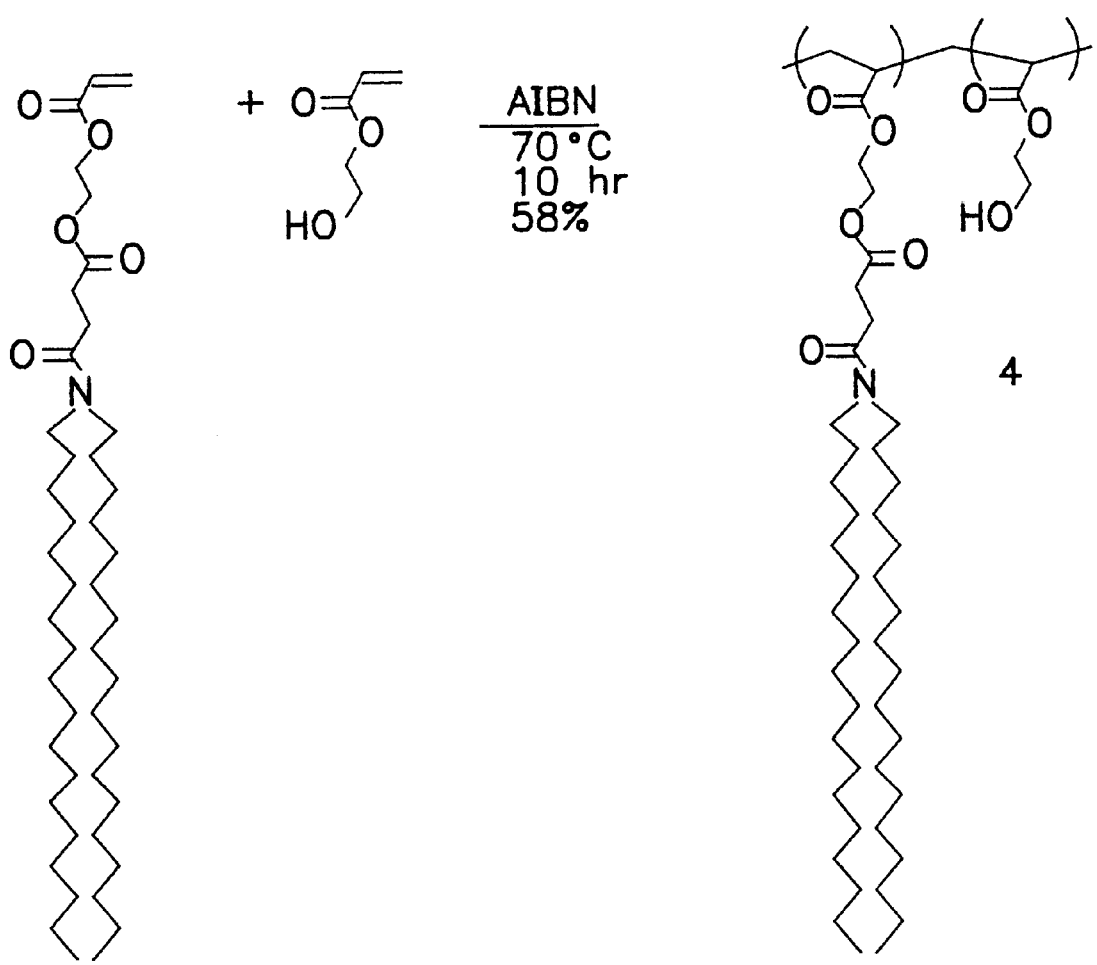
FIG. 8 is a scheme illustrating the preparation of an amphiphilic copolymer.

In a further embodiment of the invention, alginate/amphiphilic copolymer/polymerized phospholipid film was prepared. The dried substrates were opaque films that adhered to glass coverslips. After a one hour fusion at 40° C. and a three hour polymerization at 70° C., the films remained adhered to the glass (see schematic in FIG. 8). Contact angles were measured (Table 12). The initial alginate surface is completely wetted by water, indicating a highly hydrophilic surface. After coating with the amphiphilic copolymer (6), the contact angles indicated a hydrophobic surface. It is energetically favorable for the hydrophobic octadecyl chains to align at the hydrogel surface, and the contact [angles are indicative of a hydrocarbon surface] angle data suggest that the hydrocarbon chains self-assemble at the gel surface as a monolayer. The contact angles of the alginate coated with the copolymer are comparable to the contact angles of the pure copolymer (Table 12). Notably, the films remained hydrophobic after six weeks in an aqueous environment. The phospholipid-polymerized surface demonstrated hydrophilic contact angles, indicating a phosphorylcholine surface. These contact angle results indicate that a hydrophilic alginate surface was transformed to a hydrophobic alkyl chain surface, and then altered once more to a hydrophilic PC surface. In a previous embodiment, polymerized PC surfaces on an alkylated glass substrate demonstrated biocompatibility properties. In this embodiment, the substrate was changed to one that modifies drug delivery properties.

TABLE 12

Contact Angle Results.

| | Advancing | Receding |
|---|---|---|
| Alginate | wets surface | wets surface |
| Copolymer (6) | 101 ± 8 | 79 ± 6 |
| Alginate/Copolymer (6) | 94 ± 5 | 63 ± 7 |
| Alginate/(6)/PC* | 47 ± 8 | 26 ± 7 |

*After one week in air, contact angles for Alg/Cop/PC = 78 ± 5/50 ± 2.

The stability of the alkylated surface coating likely represents the formation of chain entanglements between the HEA component of the copolymer and the alginate polysaccharide. It is speculated that the entanglements are produced during the period of solvent evaporation which follows coating of the hydrogel with the HEA-AOD copolymer. As has been reported for other polymeric systems, the generation of a stable surface-localized interpenetrating network may occur due to the presence of a solvent which facilitates the migration of mutually soluble polymer segments from the solution phase into the surface of a swollen polymeric material. After the solvent is removed or replaced with a non-solvent, the collapse of the swollen interface entraps the copolymer chains. Entanglements limit the desorption of the copolymer after rehydration.

After vesicle fusion and in situ polymerization of the deposited phospholipid monolayer, initial surface characterization was performed using contact angle goniometry (Table 12). Average advancing and receding water contact angles of 47° and 26°, respectively, were observed. As such, the hydrophilicity of the film was confirmed, particularly when compared to the base substrate. In addition, an average hysteresis of 21° was noted. Hysteresis, defined as the difference between advancing and receding contact angles, is indicative of kinetic and thermodynamic film properties. For example, surface roughness and chemical heterogeneity, either intrinsically or due to molecular reorientation after penetration of water into the polymer film, may lead to large hysteresis values. In this regard, it bears reemphasis that advancing and receding angles measure the contact of water on dry and pre-wetted surfaces, respectively. Thus, hysteresis values in our polymer system likely represent, at least in part, the reorientation of hydrophilic phosphorylcholine moieties in order to minimize the free energy at the solid-water interface. Contact angle values were similar to those noted for polymerized phospholipid monolayers formed on either OTS/glass (64/44°) or on an amphiphilic terpolymer adsorbed to gold (58/31°). Marra, K. C.; Winger, T. M.; Hanson, S. R.; Chaikof, E. L. *Macromolecules* 30, 6483 (1997); Marra, K. C.; Kiddani, D. D. A.; Chaikof, E. *Langmuir* 13, 5697 (1997). In summary, contact angle data confirms that a hydrophilic alginate surface was transformed to a hydrophobic substrate of assembled alkyl chains by physical adsorption of an amphiphilic copolymer. Subsequent alteration to a phosphorylcholine surface with expected hydrophilic properties was produced by free radical polymerization of assembled phospholipid monomers.

To further characterize the surface, ESCA measurements were carried out (Table 13).

TABLE 13

| | ESCA results (45° C.) | | | | |
| --- | --- | --- | --- | --- | --- |
| | C | O | N | P | Si |
| Pure Alginate | 75.2 ± 2.1 | 17.9 ± 3.9 | — | — | 0.8 ± 0.6 |
| (Theoretical %) | 50 | 50 | — | — | — |
| Copolymer (6) | 75.4 ± 2.0 | 21.7 ± 1.8 | 1.9 0.1 | — | 1.0 ± 0.3 |
| (Theoretical %) | 84.7 | 13.6 | 1.7 | — | — |
| Alginate/(6) | 80.4 ± 1.7 | 16.1 ± 2.3 | 1.2 0.1 | — | 2.3 ± 0.6 |
| (Theoretical %) | 74.7 | 24.1 | 1.2 | — | — |
| Alginate/(6)/PC | 71.1 ± 4.4 | 24.0 3.0 | 1.9 ± 0.9 | 0.6 ± 0.3 | 2.4 ± 1.5 |
| (Theoretical %) | 75.4 | 22.4 | 1.5 | 0.7 | — |

Theoretical composition was calculated by atom counting. The results from the copolymer film were close to the theoretical percentages. [Although a small amount of the glass substrate was detected, the alginate/copolymer film was close to the theoretical percentages based on the carbon to nitrogen ratio (62% calculated vs. 66% measured).] Assuming 2.5 alkyl chains of the AOD monomer per phospholipid unit, expected atomic percent surface concentrations were calculated. This approximation was derived from a consideration of the self-organization of octadecyl alkane chains on gold substrates and the packing density of dipalmitoylphosphatidylcholine molecules within a supported monolayer on an alkylated surface. Winger T M, Chaikof E L. Synthesis and characterization of supported bioactive lipid membranes. In: *Materials Science of the Cell*, A. Plant and V. Vogel, (Ed.), MRS Publications, Pittsburgh (1998). Although a small amount of the glass substrate was detected, as demonstrated by the presence of Si, the atomic percent composition of the alginate/copolymer film approximated anticipated atomic concentrations. For example, the measured C/N ratio of 62.2 compares favorably with the predicted ratio of 67. Formation of a polymerized lipid monolayer was confirmed by the presence of both phosphorus and nitrogen. Overall, ESCA has been used infrequently in the characterization of PC based surfaces. Finally, results for the phospholipid surfaces displayed atomic concentrations very close to theoretical percentages.

Figure 9:
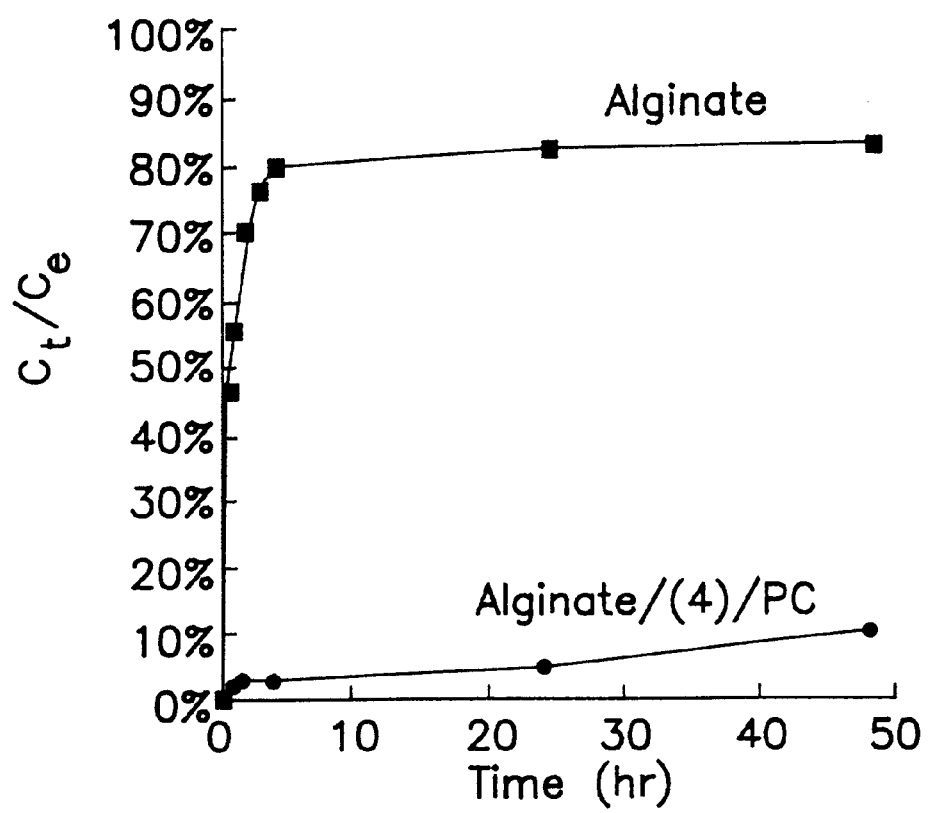
FIG. 9 is a scheme illustrating the BSA transport behavior.

Alginate beads (average diameter 2.32 mm) loaded with bovine serum albumin were coated in similar fashion with a copolymer supported lipid membrane. BSA transport behavior is presented in FIG. 9. As demonstrated, the presence of a polymerized lipid membrane significantly reduced BSA diffusivity. After 24 hours over 80% of the albumin had been released from uncoated alginate beads. In contrast, approximately 95% of the albumin was retained in coated beads. Specifically, diffusivity of BSA through the alginate/aqueous interface was reduced from $3.42 \times 10^{-4}$ $cm^2/hr$ to $2.25 \times 10^{-16}$ $cm^2/hr$ by the addition of a membrane-mimetic coating. Similarly, the overall mass transfer coefficient for BSA through polymer coated alginate beads was $4.71 \times 10^{-9}$ cm/min which was significantly less than that demonstrated by either Matthew et al. (Matthew, H. W.; Salley, S. O.; Peterson, W. D.; Klein, M. D. *Biotechnol Prog* 9, 510 (1 993)) for standard poly-L-lysine-alginate capsules ($1.5 \times 10^4$ cm/min) or by Crooks et al. (Crooks, C. A.; Douglas, J. A.; Broughton, R. L.; Sefton, M. V. *J Biomed Mater Res* 24, 1241 (1990)) for microcapsules composed of a hydroxyethylmethacrylate-methyl methacrylate copolymer ($4.21 \times 10^{-6}$ cm/min). The calculations are based upon an assumed film thickness of 125 Å for the combined amphiphilic copolymer (HEA:AOD)/polymerized phospholipid film. This approximate value is based upon ellipsometric measurements of related films including, polymerized lipid monolayers supported on a self-assembled monolayer of octadecylthiol or on an amphiphilic terpolymer of HEA:AOD:MTEM bound to a gold substrate. Marra, K. C.; Kiddani, D. D. A.; Chaikof, E. *Langmuir* 13, 5697 (1997). It is noteworthy that Monshipouri et al. (Nonshipouri, M., Rudolph, A. S. *J Microencapsulation* 12, 117 (1995)) have reported the encapsulation of alginate in lipid vesicles. Using standard extrusion techniques, particles were produced with an average diameter of 800 nm. The presence of a non-polymerized lipid membrane reduced the release of cytochrome-c from the alginate core. Nonetheless, liposomes are of limited size and, characteristically, unstable at diameters which would be required for cell encapsulation. In the design of an immunoisolation barrier an accepted standard for MWCO does not currently exist. However, these studies demonstrate that an ultrathin polymeric membrane-mimetic coating can yield a stable interface which is likely impermeable to immunoglobulins.

Several strategies have been described for the production of a membrane-like film on a hydrophilic polymer cushion. As previously noted, while deposition of a lipid film by trough techniques is feasible, it is also somewhat cumbersome, difficult or impossible to adapt to non-planar geometries, and as a non-covalently associated assembly inherently unstable for most practical applications. As alternate approach, supported membranes that are separated from the surface of gold-coated substrates by an amphiphilic terpolymer which consists of HEA, AOD, and 2-(methylthio)ethyl methacrylate, (MTEM) have also been produced. The sulfur-containing methacrylate monomer binds to gold as an anchor, whereas the hydrophilic HEA component acts as a "cushion", facilitating self-assembly of the AOD alkyl chains at the solid-liquid interface. Applicants have recently extended this work and created stabilized phospholipid monolayers by a strategy of vesicle fusion with subsequent in situ polymerization. Polymerized lipid assemblies have been produced on self-assembled monolayers of octadecyl mercaptan bound to gold, octadecyl trichlorosilane on glass, and on an amphiphilic terpolymer of HEA: AOD: MTEM (6:3:1) adsorbed to a gold coated silicon wafer. Applicants have modified the amphiphilic polymer and the deposition strategy so as to facilitate adsorption and subsequent entanglement of the HEA component into a hydrogel substrate. Anticipated physiochemical properties of the overlying membrane-mimetic monolayer were confirmed by ESCA and contact angle measurements. The ability of this thin film to significantly reduce interfacial mass transfer was documented in BSA loaded alginate beads by diffusion studies. Inherently, the modular nature of this platform provides an enhanced degree of flexibility with respect to possible incorporation of additional peptide or carbohydrate lipophilic conjugates or transmembrane pores, transporters or template forming guests for further alteration of surface or transport properties. Modification of the coating and polymerization methodologies so as to accommodate conditions required to maintain encapsulated cell viability are being investigated.

In particularly preferred embodiments, the biocompatible materials of the present invention cause little or no platelet activation adhesion. Thus, there is little thrombosis that can occur.

Substrates to which the phospholipid can be bound in accordance with the invention include any synthetic or natural material that is insoluble in physiological fluids. It can be a metal such as titanium or stainless steel, a glass such as soda glass and silica glass, an inorganic material, or an organic polymer. Preferably, it is an organic polymer, e.g., a hydrated biological material such as a polysaccharide, protein, hydrogel, etc., that has demonstrated its relative biocompatibility for use in various medical devices, e.g, surgical equipment, vascular grafts, implants and the like, as well as for use in artificial membrane systems and in drug delivery applications. Examples of polymeric substrates useful for the invention are synthetic polymers such as polyurethanes, polycarbonates, silicon elastomers, polypropylene, polyethylene, polyvinyl chlorides, polyesters, nylons, polyvinyl pyrrolidones, polymethacrylates such as polymethylmethacrylate (PMMA), n-Butyl cyanoacrylate, polyvinyl alcohols, cellulosics, polyvinylidene fluoride (PVDF), polytetrafluroethylene, polytetrafluorethylene (polyester), ethylene tetrafluoroethylene copolymer (ETFE), acrylonitrile butadiene ethylene, polyamide, polyimide, styrene acrylonitrile, and the like.

Preferably, the phospholipid moiety attached to the biocompatible materials of the present invention contains a phosphorylalkylamino group, and more preferably a phosphorylcholine polar group, as well as variable lengths of fatty acid chains, i.e., phospholipids that are derivatives of phosphatidylcholine. Particularly preferred phospholipid moieties are represented by the following structure (II):

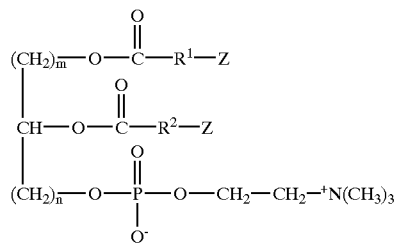

wherein $R^1$ is a $(C_1-C_{30})$alkyl group;
$R^2$ is a $(C_1-C_{30})$alkyl group;
m is 1–4;
n is 1–4; —H or

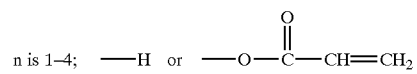

Z is such that if $R^1$ is attached to Z=—H, then $R^2$ is attached to Z=

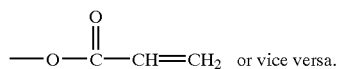

Most preferably, $R^1$ is a $(C_{12}-C_{20})$alkyl group, $R^2$ is a $(C_8-C_{14})$alkyl group, and m and n are 1.

It should be understood that this representation does not mean that there is only one phospholipid moiety attached to the substrate. Rather, phospholipid moieties are present on the substrate in an amount effective to improve the non-thrombogenic characteristics of the substrate surface. Furthermore, it should be understood that the biocompatible materials of the present invention can include one or more types of phospholipid moieties attached to the same substrate, i.e., more than one type of phospholipid moiety can be affixed to any one substrate surface.

The biocompatible biomaterial of the present invention is utilized in various medical applications including, but not limited to: (a) surgical implants, prostheses and any artificial part or device that replaces or augments a natural body part; (b) medical devices and equipment, for example, catheters, sutures, membranes, transfusion devices, blood fillers, blood pumps, blood temperature or internal blood pressure monitors, bone growth stimulators, breathing connectors, cannulae, grafts, stents, shunts, implants, ocular lenses, leads, lead adapters, lead connectors, dilators, dialyzers, probes, electrodes, sensors, and the like. Further applications for the biocompatible biomaterial of the present invention include use in the preparation of artificial membrane systems, in drug delivery, and the like.

An additional feature of the present invention is the ability to package in a kit form the chemical reagents necessary for the easy or routine preparation of a biocompatible biomaterial. By means of a kit, the self-assembly of phospholipid molecules occurs and is followed by the in situ polymerization reaction just prior to use. The kit provided by the present invention for formation of a stable biocompatible biomaterial suitable for medical application comprises an acryloyloxy-containing phospholipid moiety having a structure according to the general structure (I), and preferably structure (II), in addition to a chemical reagent for initiating in situ polymerization. A biocompatible biomaterial of the invention is prepared from such a kit by following the methods and guidance provided in the instant invention.

All publications, patent applications and patents cited herein are incorporated by reference in the same extent as if each individual publication, patent application or patent were specifically and individually indicated to be incorporated by reference.

It will be apparent to those of ordinary skill in the art that alternative methods, reagents, procedures and techniques other than those specifically detailed herein can be employed or readily adapted to practice the methods of this invention. Such alternative methods, reagents, procedures and techniques are within the spirit and scope of this invention.

The methods of this invention are further illustrated in the following non-limiting Examples. All abbreviations used herein are standard abbreviations in the art. Specific procedures not described in detail in the Examples are well-known in the art.

EXAMPLES

Example 1

Sources of Materials

Materials. AAPD (2,2'-azobis(2-methylpropionamidine) dihydrochloride), DTBC (2,6-di-tert-butyl-p-cresol), 1.12- dodecanediol, pyridine, DMAP (4-(NDN-dimethylamino) pyridine), DCC (dicyclohexylcarbodiimide), succinic anhydride, MTEM [2-(methylthio)ethyl methacrylate], and PDC (pyridinium dichromate) were obtained from Aldrich and used as received. 2-Hydroxyethyl acrylate (Aldrich) was vacuum distilled. Dioctadecylamine (Fluka) was used as received. 1-Palmitoyl-2-hydroxy-sn-glycero-3-phosphocholine was obtained from Avanti Polar Lipids and used as received. THF, toluene, dichloromethane and pyridine were obtained from Fisher and dried over 4 Å molecular sieves. Acryloyl chloride was obtained from Aldrich and vacuum distilled prior to use. Chloroform (Aldrich) was washed with water, dried over $CaCl_2$, distilled, and stored over 3 Å molecular sieves. AIBN (2,2'-azobisisobutyronitrile) (Aldrich) was recrystallized from methanol. The resin AG 501-X8 was obtained from Bio-Rad and used as received. Glass coverslips were purchased from Baxter.

Example 2

Methods of Synthesis
(a) Synthesis of 12-(Acryloyloxy)-1-dodecanol (1).

The synthesis was carried out essentially as described in Sells et al. (1994) Macromolecules 27:226.

1,12-Dodecanediol (50.0 g, 0.247 mol) was dissolved in 500 ml TBF with gentle heating. Pyridine (8.0 ml, 0.100 mol) was added and the solution was cooled to room temperature. One crystal of 2,6-di-tert-butyl-p-cresol was added. Acryloyl chloride (6.0 ml, 0.074 mol) was dissolved in 40 ml TBF and slowly added dropwise. After 24 hours, the mixture was filtered to remove pyridine hydrochloride. The filtrate was rotoevaporated to give a white solid, which was taken up in 200 ml $CHCl_3$ and placed in an ice bath for one hour. The mixture was filtered to remove unreacted diol and the filtrate was dried over $Na_2SO_4$. The solvent was removed in vacuo to give a residue that was purified by flash chromatography on silica gel ($CHCl_3$/MeOH, 95/5). The product was a clear oil (1) [yield 14.90 g (79%); $^1$H NMR ($CDCl_3$) δ 6.35–6.41 (d, vinyl, $^1$H); 6.10–6.20 (q, vinyl, 1H); 5.74–5.78 (d, vinyl, 1H); 4.10–4.18 (t, $OCOCH_2$, 2H); 3.61–3.65 (t, $HOCH_2$, 2H); 1.62–1.66 (br, $CH_2$, 4H); 1.26 (s, $CH_2$, 16H); HRMS calculated (FAB) 263.2198; observed 263.2203 (+Li)].

(b) Synthesis of 12-(Acryloyloxy)-1-dodecanoic Acid (2).

The procedure of Sells et al. (1994) Macromolecules 27:226 was used for the synthesis. Briefly, 12-(acryloyloxy)-1-dodecanol (2.24 g, 8.75 mmol) was dissolved in 5.0 ml DM and was slowly added to a mixture of PDC (10.60 g, 28.00 mmol), one crystal of 2,6-di-tert-butyl-p-cresol, and 15.0 ml DMF at 0°C. The reaction slowly reached room temperature. After 23 hours, the mixture was poured into 100 ml $H_2O$ and extracted five times into ether. The combined organic layers were washed with water and dried over $Na_2SO_4$. The solvent was removed in vacuo to give a residue that was purified by flash chromatography on silica gel ($CHCl_3$/MeOH, 97/3). The product was a white solid (2) [yield 1.07 g. (46%); mp 30.0–31.0°Cl; $^1$H NMR ($CDCl_3$) δ 6.36–6.42 (d, vinyl, 1H); 6.12–6.22 (q, vinyl, 1H); 5.75–5.82 (d, vinyl, 1H); 4.10–4.20 (t, $OCOCH_2$, 2H); 2.25–2.43 (t, $HOOCCH_2$, 2H); 1.61–1.63 (br, $CH_2$, 4H); 1.27 (s, $CH_2$, 14H); HRMS calculated (FAB) 277.1991; observed 277.1997 (+Li)].

(c) Synthesis of 1-Palmitoyl-2-[12-(acryloyloxy) dodecanoyl]-sn-glycero-3-phosphocholine (3).

The synthesis was performed essentially as described in Sells et al. (1994) Macromolecules 27:226. Briefly, to a mixture of 1-palmitoyl-2-hydroxy-sn-glycero-3-phosphocholine (0.40 g, 0. 82 mmol), 12-(acryloyloxy)-1-dodecanoic acid (0.46 g, 1.70 mmol), DMAP (0.10 g, 0.82 mmol), and one crystal of 2,6-di-tert-butyl-p-cresol, were added 6.0 ml dry $CHCl_3$. To the mixture, DCC (0.20 g, 0.98 mmol) was added, and the reaction stirred in the dark under argon. After 66 hours, the dicyclohexylurea was filtered off and washed with $CHCl_3$. The filtrate was evaporated and the residue was dissolved in 20.0 ml MeOH. Bio-Rad AG 501-8X (5.0 g) was added and the reaction stirred at room temperature for one hour. The resin was filtered and washed with MeOH. The filtrate was dried over $Na_2SO_4$. The solvent was removed in vacuo to give a residue that was purified by flash chromatography on silica gel ($CHCl_3$/MeOH, 9/1, then $CHCl_3$/MeOH/$H_2O$ (65/25/4). The product was a clear oil obtained from the second fraction (3) [yield 0.32 g (53%); $^1$H NMR ($CDCl_3$) δ 6.22–6.28 (d, vinyl, 1H); 5.88–6.12 (q, vinyl, 1H); 5.59–5.68 (d, vinyl, 1H); 5.07 (s, $POCH_2CH$, 1H), 4.24–4.44 (m, $POCH_2CH$, $HCCH_2OCO$, 4H); 410 (m, br, $CH_2OCOCH=CH_2$, 2H); 3.85–3.97 (m, $NCH_2CH_2O$), 4H); 3.07 (s, $(CH_3)_3N+$, 9H); 2.16–2.20 (m, $OOCCH_2$, 4H); 1.45 (br, $CH_2$, 6H); 1.12 (s, $CH_2$, 38H); 0.73 (t, $CH_2CH_3$, 3H); HRMS calculated (FAB) 748.5129; observed 748.5099 (+H)].

(d) Synthesis of 3-Acryloyl-3-oxapropyl-3-(N,N-dioctadecylcarbamoyl)propionate (AOD) (4).

Dioctadecylamine (2.08 g, 4.0 mmol), succinic anhydride (0.80 g, 8.0 mmol), and pyridine (0.36 ml, 8.0 mmol) were refluxed in $CH_2Cl_2$ for 46 hours. The reaction mixture was washed twice each with 2N $H_2SO_4$, $NaHCO_3$, then $H_2O$. After drying with $Na_2SO_4$, the solvent was removed in vacuo to give a residue that was recrystallized with acetone to give 1.02 g (41%) of white solid (2). To 0.88 g (1.42 mmol) of 2 was added DMAP (6.0 mg, 0.05 mmol) and 2-hydroxyethyl acrylate (0.3 ml, 2.62 mmol) in 20 ml $CH_2Cl_2$ at 0° C. DCC (0.32 g, 1.55 mmol) in 9 ml $CH_2Cl_2$ was added dropwise. After one hour at 0° C., the reaction was stirred overnight at room temperature under Ar. The reaction mixture was suction filtered to remove dicyclohexylurea. The filtrate was washed with water then dried over $Na_2SO_4$. The solvent was removed in vacuo to give a residue that was purified by flash chromatography on silica gel (hexanes:ethyl acetate:$CH_2Cl_2$, 5:1:1). The product was a clear oil that slowly solidified (4) [yield 0.63 g (27%); mp 31.0–32.0° C.; $^1$H NMR ($CDCl_3$) δ: 6.35 (d, vinyl, 1H); 6.09 (q, vinyl, 1H); 5.80 (d, vinyl, 1H); 4.28 (s, $CH_2OOC$, 4H), 3.17–3.23 (m, $CH_2O$, $CH_2N$, 4H), 2.50–2.60 (m, $CH_2COO$, 4H), 1.20 (br, $CH_2$, 60H); 0.82 (t, $CH_3$, 6H) ppm; HRMS calculated (FAB) 726.6588; observed 726.6599 (+Li)].

(e) Synthesis of Terpolymer (5) by Polymerization of HEA+ AOD+MTEM.

2—Hydroxyethyl acrylate (HEA) (0.08 g, 0.70 mmol), 2-(methylthio)ethyl methacrylate (MTEM) (0.02 g, 0.12 mmol) and acrylate 4 (AOD), (0.25 g, 0.35 mmol) were dissolved in 1.5 ml Toluene. AIBN (2.8 mg, 0.01 mmol) was added. The solution was purged with Ar, sealed, and placed in a 70° C. oil bath for 18 hours. The solution was cooled to room temperature then was slowly added to 50 ml MeOH. The white precipitate was recovered and dried to give polymer 5 [yield 0.06 g (17%); Molecular weight determined by GPC:$M_w$=19248 g/mol, PDI=2.16; $^1$H NMR ($CDCl_3$) δ; 4.12–4.26 (m, $CH_2OOCO$), 3.79 (t, $CH_2OH$), 3.23 (m, $CH_2O$, $CH_2N$), 2.62–2.73 (m, $CH_2S$, $CHCOO$, $CH_2COO$), 2.16 (s, $CH_3S$), 1.70 (s, $CH_3C$), 1.45–1.65 (m, $CH_2CHCOO$) 1.30 (br, $CH_2$'s), 0.88 (t, $CH_3$) ppm].

(f) Synthesis of Copolymer (6) by Polymerization of HEA+ AOD.

2—Hydroxyethyl acrylate (0.018 g, 0.15 mmol), and acrylate 4 (AOD), (0.11 g, 0.15 mmol) were dissolved in 1.0 ml toluene. AIBN (1.0 mg, 0.006 mmol) was added. The solution was purged with Ar, sealed and placed in a 70° C. oil bath for 18 hours. The solution was cooled to room temperature, then was slowly added to 25 ml of methanol. The white precipitate was recovered and dried to give polymer 6 [yield 0.70 g (58%); molecular weight determined by GPC: $M_w$=8679 g/mol, PDI=2.29].

Example 3

Preparation of Silanized Glass (i) Materials

Microscope borosilicate glass coverslips (S/P Cover Glass, 24×40×0.25 mm, no. 2 thickness) were purchased from Baxter Scientific, Inc. Multi-Terge™, a powerful high-pH chelating detergent, was purchased from EM Diagnostic Systems, Inc. (Gibbstown, N.J.). All other chemicals and solvents (HPLC grade) were purchased from Aldrich. Hydrated $CHCl_3$ was prepared and stored in a clean screw-cap amber bottle by vigorously shaking 25 ml $CHCl_3$ (1% ethanol-stabilized) with 10 $\mu l$ deionized water. A 63 mM octadecyltrichlorosilate (OTS) stock solution in dry $CCl_4$ was prepared under nitrogen by injecting 1.7 ml OTS (95%, stored in dessicator at room temperature) with a 3-ml polypropylene syringe through a 0.1 $\mu m$ PTFE syringe filter, directly into the commercial Suresea™ container of 100 ml anhydrous $CCl_4$ (99+%, <0.005% water). The bottle was capped with a virgin rubber liner (Aldrich), closed with a bakelite screw-cap, and sealed with parafilm for long-term storage at room temperature. Liquid volumes below 30 ml were measured using non-lubricated polypropylene syringes (Aldrich). Dust-Off XL™ puff-duster cans (compressed gas filtered to 0.1 $\mu m$) were purchased from Falcon Safety Products, Inc. (Branchburg, N.J.).

(ii) Method.

Monolayers of OTS on atomically smooth glass coverslips were prepared according to a protocol derived from previously published methods (Calistri-Yeh et al., *Langmuir* [1996] 12:2747; Siedlecki et al. [1994] Biomed. Mater. Res. 28:971; Balachander et al. [1990] Langmuir 6(11):1621; Sabatani et al. [1987] J. Phys. Chem. 91:6663; Wasserman et al. [1989] J. Am. Chem. Soc. 111:5852; Maoz et al. [1984] J. Colloid Interface Sci. 100(2):456; Bierbaum et al. [1995] Langmuir 11:512; Parikh et al. [1994] J. Phys. Chem. 98:7577; and xiao et al. [1995] Langmuir 11(5):1600) and adapted for large scale sample production. A typical single batch yielded 54 homogeneously coated hydrophobic slides.

In the preparation of alginate/amphiphilic copolymer/polymerized phospholipid film, 1.0 ml alginate in 9% saline solution was cast onto a glass coverslip. To initiate polymerization, 0.5 ml 1.1% $CaCl_2$ (pH 7.1) was added. The film dried at room temperature for 15 minutes, then was rinsed with 0.58% $CaCl_2$ (pH 7.1), then 0.28% $CaCl_2$ (pH 7.1), and finally rinsed with 0.9% saline. To coat with the amphiphilic copolymer (6), a 28 mM THF solution of the polymer was cast onto the alginate film. The film was dried under vacuum overnight. Vesicle preparation and fusion was carried out as previously described. The vesicles were fused for one hour at 40° C. Free radical initiator AAPD (10% mol) was added. After purging with argon, polymerization was carried out at 70° C. for three hours. The film was cooled to room temperature, then rinsed with doubly distilled water. Surface characterization was then carried out.

Specifically, commercial coverslips were cut longitudinally into two slabs of 12×40×0.25 mm with a diamond pen, puff-dusted, and transferred to a Class 10 cleanroom. Two 400-ml glass beakers and one 200-ml amber glass bottle were then simultaneously degreased and deionized by application of a solution of Multi-Terge/$H_2O$ 1:8 with a camel hair brush, followed by copious rinsing with running deionized water, and allowed to dry in open air, occasionally blowing with a nitrogen gun. The precleaned containers were subsequently etched under argon in a Harrick barrel plasma etcher (9 min, 100 Watts, 500 m Torr Ar). All 54 coverslips were precleaned (both sides) and etched similarly, and mounted in a Teflon dip basket which was specifically designed for the purpose of 1)allowing quick handling of a large batch of slides, 2) enabling full exposition of the front and back sides of the coverslips to the reaction medium, and 3) minimizing the coverslip surface-to-solvent ratio in the reaction vessel. A mixture of 24.8 ml hydrated $CHCl_3$, 248 ml bicyclohexyl, and 27.0 ml of a 62.5 mM OTS stock solution in dry $CCl_4$, (filtered through a 0.1 $\mu m$ PTFE syringe filter, Whatman), was well shaken in the above 200 ml screw-capped amber bottle. and poured into the 400 ml clean beaker. The basket was fully immersed into this reaction mixture within five minutes of mixing. OTS deposition was allowed to proceed at room temperature in open air without agitation. After one hour, the basket was lifted out of solution, rinsed by dipping in 2×300 ml of HPLC-grade $CHCl_3$, and sonicated (approximately 47 kHz, approximately 130 W) in 2×300 ml $CHCl_3$ for ten minutes each. The basket was then copiously rinsed with running deionized water and blown dry with a nitrogen gun. Finally, the slides were taken out, one by one with stainless steel forceps, and stored in wafer shippers (Fluoroware, Inc., Chaska, Minn.) interlayered with lint-free cleanroom tissue. For use in subsequent experiments, the OTS-coated slides were further cut to the appropriate size and puff-dusted.

Example 4

Preparation of Vesicles and Fusion

A stock solution of the phospholipid in MeOH/$CHCl_3$ (1/1) was stored in the freezer and used throughout the experiments. One ml of the solution was added to a pre-weighed vial, and the solvent was removed by gentle blowing with an argon stream. The film (4–10 mg) was dried in the SpeedVac at room temperature for one hour, then used immediately for vesicle preparation. Sodium phosphate buffer solution (20 mM) was added to the film in the vial. The vial was stoppered and sonicated for one minute. Vesicles were then prepared by a freeze-thaw method. The cloudy solution was heated to 50° C. in a hot water bath, vortexed for one minute, then frozen in liquid nitrogen. This procedure was repeated three times, and the multilamellar vesicles were then extruded through 2000 nm, 600 nm, and 200 nm polycarbonate filters successively (MacDonald et al. [1991] Biochim. Biophys. Acta 1061:297). Fusion onto an alkylated glass coverslip consisted of diluting the unilamellar vesicles with buffer to the appropriate concentration, and pouring the vesicle solution onto an alkylated slide. Fusion was initiated by addition of NaCl (750 mM buffered saline, pH 6.2) solution. The system was then kept in the dark, static, under argon, at either room temperature or 40° C., for specified amounts of time.

Example 5

Polymerization

After vesicle fusion was complete, 0. 14.0 mg of initiator was added to the system. The test tube containing the slide and buffer solution was stoppered and purged thoroughly with argon. The system was sealed and placed in an oil bath at 70° C. or subjected to UV light for varying amounts of time. After polymerization was complete, the solution was pipetted from the tube, and the cover slip was rinsed 20–30 times with deionized water. The film was stored in water until further surface characterization.

Example 6

Instrumentation

Contact angles were measured on a Rame-Hart goniometer, Model 100-00. The values reported are an average of at least five readings. Proton NMR data was obtained on a QE300 instrument. Angle-dependent ESCA data were obtained using a Physical Electronics (PHI) Model 5100 spectrometer equipped with a Mg/Ti dual-anode source and an Al/Be window. The system uses a hemispherical analyzer with a single-channel detector. Mg KαX-rays (1253.6 eV) were used as an achromatic source, operated at 300 W (15 kV and 20 mA). The base pressure of the system was lower than $5 \times 10^{-9}$ Torr, with an operating pressure no higher than $1 \times 10^{-7}$ Torr. A pass energy of 89.45 eV was used when obtaining the survey spectra, and a pass energy of 35.75 eV was used for the high-resolution spectra of elemental regions. Spectra were obtained at the following take-off angles: 15, 45, and 90°. The instrument was calibrated using Mg KαX-radiation: the distance between Au $4F_{7/2}$ and Cu $2P_{3/2}$ was set at 848.67 eV, and the work function was set using Au $4F_{7/2}$ and Cu $2p_{3/2}$ and checked using Au $3d_{5/2}$. All metals were sputter cleaned to remove oxides. Full width at half-maximum for Ag $3_{d3/2}$ was measured to be 0.8 eV at a count rate of 30,000 counts.

GPC results were obtained using a Waters 590 programmable HPLC pump, a Waters 410 differential refractometer maintained at 40° C., a Waters 745 data module, and 2 narrow-bore Phenogel columns (linear pore size and 500 Å, Phenomenex) in series maintained at 35° C. Molecular weights are relative to monodisperse polystyrene standards. The solvent was THF. Ellipsometry data was obtained on a PlasMos ellisometer, model SD2300. Chromium (approximately 200 Å), then gold (approximately 2000 Å) were evaporated onto the silicon wafer using a CVC Products e-beam evaporator, model SC-5000. Gold surfaces were cleaned using a Plasma-Therm RIE, model WAfrtBatch 720/740.

Example 7

Shear Flow Studies

Adherence assays were performed at a continuous shear stress of 200 dyn/cm² in a parallel plate flow chamber, as previously described (Brittain et al. [1992] J. Lab. Clin. Med. 112:528; Wick et al. [1987] J. Clin. Invest. 80:905). The shear stress was held constant using a syringe pump (Harvard Apparatus, Southnatick, Mass.) and the temperature was maintained at 37° C. with the aid of a water bath (Nicholson Precision Instruments, Bethesda, Md.).

Example 8

Baboon Model: Arteriovenous Shunt

In vivo studies were performed as described in Hanson et al. (1985) Arteriosclerosis 5:595. Briefly, glass tubes (4 mm i.d.×3 cm) were alkylated and in situ lipid polymerization performed as described above. Glass tubes were interposed into a permanent Silastic arteriovenous shunt which had been surgically implanted between the femoral artery and vein in male Baboons (*Papio anubis*). Circulating platelet concentrations averaged 391,000 platelets/µl. Ketamine hydrochloride (10 mg/kg intramuscularly) was given as a preanesthetic agent, and the operation was performed under general 1% halothane anesthesia. All procedures were in accordance with institutional guidelines. Mean blood flow rate through the shunt was measured continuously using a Doppler ultrasonic flowmeter and held constant by an external screw clamp at 100 ml/min.

Example 9

Platelet Radiolabelling

Autologous baboon platelets were radiolabeled on the day prior to the shunt study. Forty-five milliliters of whole blood were initially withdrawn into syringes containing 9 ml of acid citrate dextrose anticoagulant. The blood was centrifuged at 160 g for 15 minutes and the platelet-rich plasma removed and centrifuged at 1500 g for 15 minutes. The platelet pellet was then removed, washed in normal saline solution with 0.1% (w/v) dextrose, and 600 µCi of Indium-111-oxine (Amersham Co.) added to the platelet suspension. Following a 10-minute incubation at room temperature, 3 ml of platelet-poor plasma were added and the platelets incubated for an additional 2 minutes. The mix was centrifuged at 1550 g for 5 minutes to form a platelet pellet, the supernatant and excess Indium-111-oxine removed, and the platelets resuspended in 5 ml of reserved plasma. Approximately 0.5 mCi of Indium-111-oxine labeled platelets were reinjected into the baboon. Platelet function is not altered by this technique when studied by either thrombin stimulated platelet release of $^{14}C$ serotonin or by morphological studies of dense body distribution.

Example 10

Platelet Deposition Measurement

Platelet uptake on test surfaces was monitored over a 120 minute period using scintillation camera imaging of the 172 keV $^{111}In$ gamma photon peak. A high sensitivity $^{99}Tc$ collimator was utilized and images acquired with a GE 400T scintillation camera (General Electric, Milwaukee, Wis.) interfaced with a Medical Data Systems A³ image processing system (Ann Arbor, Mass.). Immediately before imaging, 2 minute images were acquired of the 200 µl sample of platelet concentrate (injection standard) and of a segment of 4.0 mm i.d. Silastic tubing filled with autologous blood and having the same luminal volume as the glass tube segment (blood standard). Images were obtained continuously with data storage at 2-minute intervals. Deposited $^{111}In$-platelet activity was calculated by subtracting the blood standard activity from all dynamic study images. Data was converted, at each time point, to total platelet deposition per unit test surface, as follows:

$$\text{Platelets/unit surface area} = \frac{[\text{Test surface activity (cpm)} - \text{Background activity (cpm)}]}{\text{Blood specific activity(cpm/ml)}} \times \text{platelets/ml} \quad (1)$$

where $$\text{Blood specific activity} = \quad (2)$$

-continued $$[\text{Blood Standard (cpm)} - \text{Background (cpm)}] \times \frac{\text{Fraction of In-111 in platelets}}{\text{Volume of the Blood Standard (ml)}}$$

Example 11

Preparation of Films

Preparation of Films: Onto a glass coverslip, 2% alginate in 0.9% saline solution was cast and hydrogel formation initiated by the addition of 1.1% CaCl$_2$ (pH 7.1). The film was dried at room temp for 15 min., rinsed with 0.58% CaCl$_2$ (pH 7.1), followed by 0.28% CaCl$_2$ (pH 7.1) and 0.9% saline. To coat with the amphiphilic copolymer (4), a 28 mM THF solution of the polymer was cast onto the alginate film. The film was dried under vacuum overnight. Unilamellar vesicle preparation and surface fusion was carried out as previously described. The vesicles were fused to the coated film for one hour at 40° C. Free radical initiator AAPD (10% mol) was added. After purging with argon, polymerization was carried out at 70° C. for 3 hrs. The film was cooled to room temp, then rinsed with doubly distilled water.

Example 12

Transport Studies (i) Protein Radiolabeling.

Bovine serum albumin (BSA; MW 69,000) was radiolabeled with $^{125}$I using Iodobeads (Pierce) following the manufacturer's protocol. Briefly, three Iodobeads were washed with 50 mM phosphate buffer 1 g 7.4) twice and dried on Whatman paper. The beads were then incubated with 1000 µCi of $^{125}$I in 200 µL of the phosphate buffer in a 1.5 mL polypropylene eppendorf tube for 5 minutes at room temperature. After the initial incubation period, 500 µL of the stock BSA solution (10 mg/mL) was added to the reaction and incubated for an additional 15 minutes at room temperature with occasional mixing. The iodination reaction was terminated by removing the beads from the reaction vessel and by desalting the mixture using a PD10 desalting column (Pierce). The concentration of radiolabeled fibronection was determined by the Bradford Protein Microassay (Bio-Rad) and the percent incorporation was determined by the use of TCA precipitation method. Specific activity of the protein solution averaged 2.40×10$^5$ cpm/µg.

(ii) Preparation of BSA-doped Alginate Beads.

To prepare 10 mL of 10:1 alginate/BSA solution, 19 mg of BSA were dissolved in 10 mL of 2% alginate in 0.9% NaCl solution. This solution was then spiked with 1 mg of radiolabeled BSA. To prepare the beads, drops of alginate/BSA solution were extruded from a 1 cc syringe through a 27 gauge needle (Becton Dickinson) and allowed to fall into 15 mL of 1.1% CaCl$_2$ from a height of 6 inches under continuous stirring. The drops immediately gelled; into spherical beads and were incubated in the 1.1% CaCl$_2$ solution for 30 minutes at room temperature in continuous stirring. The beads were then washed twice each with 0.58% and 0.28% CaCl$_2$ solution before storing in 0.9% NaCl solution. The mean radius of the beads was determined by taking videomicrographs of at least 20 individual beads using a 4× objective and 0.45× video lens and measuring the area of the largest cross-section of each bead. The radius was calculated by $$r_s = \sqrt{C\frac{A}{\pi}} \quad (1)$$

where $r_s$ is the radius of the cross-section, C is the conversion factor from pixels to µm$^2$ (51.02 µm$^2$/pixel) determined through the use of a stage micrometer, and A is the area of the cross-section in pixels.

(ii) Coating the Beads With a Membrane-mimetic Surface.

The alginate/BSA beads were initially coated with BEA/AOD polymer in a 15 mM solution in THF followed by drying for 24 hours under vacuum. The beads were then rehydrated with 0.9% NaCl solution for 24 hours and placed in a solution containing 600 nm monoacryloyl-DPPC vesicles in 20 mM phosphate buffer (pH 7.4). Vesicles were allowed to fuse with the alkylated bead surface for 30 minutes at room temperature to generate a supported lipid monolayer. Polymerization of the DPPC was initiated by adding 1 mg of AAPD and purging the sealed reaction vessel with pure argon. Polymerization was allowed to continue for 3 hours in 70° C., after which the solution was cooled to room temperature and the beads were washed three times with 0.9% NaCl. Control beads were prepared by the same method as above except without the presence of HEA/AOD polymer in the initial coating stage and without the presence of DPPC in the subsequent vesicle fusion and polymerization process.

(iv) Diffusion Assay.

Between 60 and 65 beads were placed in each 20 mL glass vial filled with 15 ml 0.9% NaCl solution. The vials were placed in a constant-temperature incubation oven equipped with a rotissery wheel to provide continuous agitation. Experiments with water-soluble dye showed that the rotation motion of the rotissery wheel provided adequate agitation to validate the well-mixed solution assumption needed for the data analysis (data not shown). The beads were incubated at 37° C. and samples were taken at regular intervals and the radioactivity counted to measure the amount of BSA diffused into the solution. The amount and the concentration of BSA remaining in the beads was calculated by mass balance. The unsteady-state diffusion of the BSA from a sphere was analyzed as described by Skelland (Skelland, A. H. P., Diffusional Mass Transfer; John Wiley & Sons, Inc., New York (1974)) and the overall mass transfer coefficient determined by a procedure similar to that utilized by Crooks et al.(Crooks, C. A.; Douglas, J. A.; Broughton, R. L.; Sefton, M. V. J Biomed Mater Res 24, 1241 (1990)).

What is claimed is:

1. A process for improving nonthrombogenic properties of a substrate surface, said process comprising forming a bilayer by:

attaching to said substrate surface a first layer comprising a hydrophilic polymer cushion and long-chain alkyl or acyl groups;

forming an outer lipid monolayer attached to said first layer by means of said long-chain alkyl or acyl groups by in situ polymerization of vesicles made of a phospholipid having a phohsphorylalkylaamino substituent and a single polymerizable substituent;

wherein said bilayer is present on said substrate in an amount and orientation effective to provide an improved nonthrombogenic surface compared to a substrate without said bilayer.

2. The process of claim 1 wherein said bilayer is non-covalently attached to said substrate.

3. The process of claim 1 wherein said phospholipid has the structure:

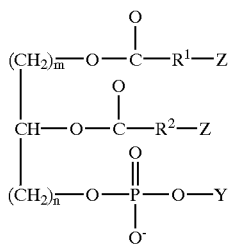

wherein $R^1$ is a $(C_1-C_{30})$alkyl group;

$R^2$ is a $(C_1-C_{30})$alkyl group;

m is 1–4;

n is 1–4;

Y is an alkylamino group; and

Z is —H or a polymerizable monomeric group such that if $R^1$ is attached to Z=—H, then $R^2$ is attached to Z=a polymerizable monomeric group, and if $R^1$ is attached to $Z_l$=a polymerizable monomeric group, then $R^2$ is attached to Z=—H.

4. The process of claim 1 wherein Z is selected from the group consisting of acryloyloxy, methacryloyl, dienoyl, sorbyl, styryl, acrylamido, acrylonitrilo, and N-vinyl pyrrolidonyl.

5. The process of claim 1 wherein

Y is —$CH_2$—$CH_2$—$^+N(CH_3)_3$ or —$CH_2$—$CH_2$—$^+NH_3$; and

Z is —H or —O—(CO)—CH=$CH_2$.

6. The process of claim 1 wherein Y is —$CH_2$—$CH_2$—$^+N(CH_3)_3$.

7. The process of claim 1 wherein $R^1$ is a $(C_{12}-C_{20})$alkyl group;

$R^2$ is a $(C_8-C_{14})$alkyl group; and m is 1 and n is 1.

8. The process of claim 1 wherein said phospholipid is 1-palmitoyl-2[12-(acryloyloxy)dodecanoyl]-sn-glycero-3-phosphorylcholine.

9. The process of claim 1 wherein said substrate is selected from the group consisting of polymer, metal, glass, a silicon wafer, a gold-coated surface, and a hydrogel.

10. The process of claim 1 wherein said substrate is a hydrogel.

11. The process of claim 10 wherein said substrate is alginate.

12. The process of claim 1 wherein said substrate is coated with octadecyltrichlorosilane or octadecylthiol.

13. The process of claim 1 wherein said first layer comprises a terpolymer or a copolymer comprising said hydrophilic polymer cushion.

14. The process of claim 1 wherein said first layer comprises an amphiphilic dialkyl-containing terpolymer.

15. The process of claim 14 wherein said terpolymer is produced from a 2-(methylthio)ethyl methacrylate monomer, a 2-hydroxyethyl acrylate monomer, and a 3-acryloyl-3-oxapropyl-3-(N,N-dioctadecylcarbamoyl) propionate monomer.

16. The process of claim 13 wherein said first layer comprises a copolymer and said copolymer is produced from a 2-hydroxyethyl acrylate monomer and a 3-acryloyl-3-oxapropyl-3-(N,N-dioctadecylcarbamoyl)propionate monomer.

17. The process of claim 13 wherein said substrate is an alginate.

18. The process of claim 1 further comprising:

preparing vesicles from said phospholipid;

depositing said vesicles on said first layer;

exposing said deposited vesicles to an initiator of polymerization such that said phospholipid undergoes in situ polymerization.

19. The process of claim 18 further comprising fusing the deposited vesicles prior to exposing them to the initiator of polymerization.

20. The process of claim 1 wherein said substrate comprises a drug, and wherein said bilayer is capable of transporting said drug therethrough.

* * * * *